US012400735B2

(12) United States Patent
Yoo et al.

(10) Patent No.: US 12,400,735 B2
(45) Date of Patent: *Aug. 26, 2025

(54) METHOD AND SYSTEM FOR PREDICTING RESPONSE TO IMMUNE CHECKPOINT INHIBITOR BASED ON A DENSITY OF IMMUNE CELLS

(71) Applicant: LUNIT INC., Seoul (KR)

(72) Inventors: Donggeun Yoo, Seoul (KR); Chanyoung Ock, Seoul (KR); Kyunghyun Paeng, Seoul (KR)

(73) Assignee: LUNIT INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/463,962

(22) Filed: Sep. 8, 2023

(65) Prior Publication Data
US 2023/0420072 A1    Dec. 28, 2023

Related U.S. Application Data

(63) Continuation of application No. 17/502,339, filed on Oct. 15, 2021, which is a continuation of application No. PCT/KR2021/005771, filed on May 7, 2021.

(30) Foreign Application Priority Data

May  8, 2020   (KR) .................. 10-2020-0055483
Apr. 27, 2021   (KR) .................. 10-2021-0054206
May  7, 2021   (KR) .................. 10-2021-0059537

(51) Int. Cl.
*G16B 20/00*    (2019.01)
*G06N 3/02*     (2006.01)

(52) U.S. Cl.
CPC .............. *G16B 20/00* (2019.02); *G06N 3/02* (2013.01)

(58) Field of Classification Search
None
See application file for complete search history.

(56) References Cited

U.S. PATENT DOCUMENTS

| | | | |
|---|---|---|---|
| 10,585,032 B2 | 3/2020 | Fukuda et al. | |
| 10,902,256 B2 | 1/2021 | Madabhushi | |
| 11,436,718 B2 | 9/2022 | Yoshida et al. | |
| 2017/0169567 A1 | 6/2017 | Chefd'hotel et al. | |
| 2017/0270346 A1 | 9/2017 | Ascierto et al. | |
| 2017/0285029 A1 | 10/2017 | Hanks et al. | |
| 2017/0352157 A1 | 12/2017 | Madabhushi et al. | |
| 2019/0287240 A1 | 9/2019 | Gaire et al. | |
| 2020/0388029 A1 | 12/2020 | Saltz et al. | |
| 2021/0343009 A1 | 11/2021 | Gaire et al. | |
| 2023/0177682 A1 | 6/2023 | Xiao et al. | |

FOREIGN PATENT DOCUMENTS

| | | |
|---|---|---|
| EP | 3 108 446 B1 | 3/2019 |
| JP | 2017-509871 A | 4/2017 |
| JP | 2017-516992 A | 6/2017 |
| JP | 2018-100976 A | 6/2018 |
| JP | 2019-95212 A | 6/2019 |
| KR | 1020030066766 A | 8/2003 |
| KR | 1020150008846 A | 1/2015 |
| KR | 101889723 B1 | 8/2018 |
| KR | 102068279 B1 | 1/2020 |
| KR | 1020200040754 A | 4/2020 |
| WO | 2015/069827 A2 | 5/2015 |
| WO | 2019/108888 A1 | 6/2019 |
| WO | 2020/083970 A1 | 4/2020 |
| WO | 2022/047412 A1 | 3/2022 |

OTHER PUBLICATIONS

Chen, Ting, and Christophe Chefd'Hotel. "Deep learning based automatic immune cell detection for immunohistochemistry images." International workshop on machine learning in medical imaging. Cham: Springer International Publishing, 2014.*

Galon, Jérôme, et al. "Type, density, and location of immune cells within human colorectal tumors predict clinical outcome." Science 313.5795 (2006): 1960-1964.*

Blankenstein, Thomas. "The role of tumor stroma in the interaction between tumor and immune system." Current opinion in immunology 17.2 (2005): 180-186.*

Jiang, Peng, et al. "Signatures of T cell dysfunction and exclusion predict cancer immunotherapy response." Nature medicine 24.10 (2018): 1550-1558.*

Xu, Jun, et al. "A deep convolutional neural network for segmenting and classifying epithelial and stromal regions in histopathological images." Neurocomputing 191 (2016): 214-223.*

Parra et al., "Validation of multiplex immunofluorescence panels using multispectral microscopy for immune-profiling of formalin-fixed and paraffin-embedded humantumor tissues", Scientific Reports, Oct. 17, 2017, vol. 7/No. 13380, pp. 1-11 (11 total pages).

Translation of the International Search Report of PCT/KR2021/005771 dated Aug. 13, 2021.

Kather et al., "Topography of cancer-associated immune cells in human solid tumors," eLife, DOI: https://doi.org/10.7554/eLife.36967, Sep. 4, 2018.

(Continued)

*Primary Examiner* — G. Steven Vanni

(74) *Attorney, Agent, or Firm* — Sughrue Mion, PLLC

(57) ABSTRACT

The present disclosure relates to a method, performed by at least one computing device, for predicting a response to an immune checkpoint inhibitor. The method includes receiving a first pathology slide image, detecting one or more target items in the first pathology slide image, determining at least one of an immune phenotype of at least some regions in the first pathology slide image or information associated with the immune phenotype based on the detection result for the one or more target items, and generating a prediction result as to whether or not a patient associated with the first pathology slide image responds to the immune checkpoint inhibitor, based on the immune phenotype of the at least some regions in the first pathology slide image or the information associated with the immune phenotype.

14 Claims, 17 Drawing Sheets

(56) References Cited

OTHER PUBLICATIONS

Extended European Search Report issued Jun. 11, 2024 in Application No. 21800694.8.
Daniel S. Chen, et al.,"Elements of cancer immunity and the cancer-immune set point", Nature, Jan. 2017, vol. 541, pp. 321-330 (10 pages).
Communication issued Jan. 28, 2025 in Japanese Patent Application No. 2022-561179.
Communication issued Feb. 18, 2025 in Japanese Patent Application No. 2022-556072.
Non-Final Office Action dated May 7, 2025 issued in U.S. Appl. No. 17/502,661.
Final Office Action dated Apr. 23, 2025 issued in U.S. Appl. No. 18/463,912.
Alessia Echarti et al., "CD8+ and Regulatory T cells Differentiate Tumor Immune Phenotypes and Predict Survival in Locally Advanced Head and Neck Cancer", Cancers, 2019, vol. 11, No. 1398, pp. 1-13 (13 pages total).
E. Lanitis et al., " Mechanisms regulating T-cell infiltration and activity in solid tumors", Annals of Oncology, 2017, vol. 28, Supplement 12, pp. xii18-xii32 (15 pages total).
Jonghanne Park et al., "Abstract 5076: Comprehensive deep learning analysis of H&E tissue phenomics reveals distinct immune landscape and transcriptomic enrichment profile among immune inflamed, excluded and desert subtypes in non-small cell lung cancer", Cancer Research, 2020, vol. 80, 16_Supplement, p. 5076 (5 pages total).
Kyunghyun Paeng et al., "Abstract 2445: Pan-cancer analysis of tumor microenvironment using deep learning-based cancer stroma and immune profiling in H&E images", Cancer Research, 2019, vol. 79, 13_Supplement, p. 2445 (5 pages total).
Sehhoon Park et al., "Deep learning-based predictive biomarker for immune checkpoint inhibitor response in metastatic non-small cell lung cancer.", Journal of Clinical Oncology, 2019, vol. 37, 15_supplement, p. 9094 (3 pages total).

\* cited by examiner

| | Cancer Type  Breast Cancer    Report Date  11/24/2020 |
|---|---|
| Total Size of Tissue | Lorem ipsum dolor sit amet, consectetur adipiscing elit. Sit at euismod dignissim quisque. |
| TCGA Pan-Carcinoma Statistics | Lorem ipsum dolor sit amet, consectetur adipiscing elit. |

ACADEMIC REFERENCES

1) Deep Convolutional Neural Network-Based Mitosis Detection In Invasive Carcinoma Of Breast By Smartphone-Based Histologic Image Acquisition Seokhwi Kim, Jungin Lee, Soo-hyun Hwang, Sooyoun Cho, Sangheum Hwang, Hyo-Eun Kim, Hyemin Shim, Miso Yang, Sangyong Song USCAP 2018

2) A Unified Framework For Tumor Proliferation Score Prediction In Breast Histopathology Kyunghyun Paeng, Sangheum Hwang, Sunggyun Park, Minsoo Kim, Seokhwi Kim MICCAI DLMIA Workshop 2017

3) Batch-Instance Normalization For Adaptively Style-Invariant Neural Networks Hyeonseob Nam, Hyo-Eun Kim NIPS 2018

4) A Robust And Effective Approach Towards Accurate Metastasis Detection And Pn-Stage Classification In Breast Cancer Byungjae Lee, Kyunghyun Paeng MICCAI 2018

5) From detection of individual metastases to classification of lymph node status at the patient level: the CAMELYON17 challenge Peter Bandi, Oscar Geessink, Quirine Manson, Marcory van Dijk, Maschenka Balkenhol, Meyke Hermsen, Babak Ehteshami Bejnordi, Byungjae Lee, Kyunghyun Paeng, Aoxiao Zhong, Quanzheng Li, Farhad Ghazvinian Zanjani, Svitlana Zinger, Keisuke Fukuta, Daisuke Komura, Vlado Ovtcharov, Shenghua Cheng, Shaoqun Zeng, Jeppe Thagaard, Anders B. Dahl, Huangjing Lin, Hao Chen, Ludwig Jacobsson, Martin Hedlund, Melih Cetin, Eren Halıcı, Hunter Jackson, Richard Chen, Fabian Both, Jorg Franke, Heidi Kusters-Vandevelde, Willem Vreuls, Peter Bult, Bram van Ginneken, Jeroen van der Laak, and Geert Litjens Transactions on Medical Imaging (TMI) 2018

6) PseudoEdgeNet: Nuclei Segmentation only with Point Annotations Inwan Yoo, Donggeun Yoo, and Kyunghyun Paeng MICCAI 2019

7) SRM : A Style-based Recalibration Module for Convolutional Neural Networks HyunJae Lee, Hyo-Eun Kim, Hyeonseob Nam ICCV 2019

8) Deep learning-based predictive biomarker for adjuvant chemotherapy in early-stage hormone receptor-positive breast cancer Soo Youn Cho, Eun Yoon Cho, Kyunghyun Paeng, Geunyoung Jung, Sarah Lee, Sang Yong Song AACR 2019

9) Pan-cancer analysis of tumor microenvironment using deep learn

1400

1500

METHOD AND SYSTEM FOR PREDICTING RESPONSE TO IMMUNE CHECKPOINT INHIBITOR BASED ON A DENSITY OF IMMUNE CELLS

CROSS-REFERENCE TO RELATED APPLICATIONS

This application is a continuation of U.S. application Ser. No. 17/502,339 filed Oct. 15, 2021, which is a continuation of International Application No. PCT/KR2021/005771 filed on May 7, 2021 which claims priority to Korean Patent Application No. 10-2020-0055483 filed on May 8, 2020, Korean Patent Application No. 10-2021-0054206 filed on Apr. 27, 2021, and Korean Patent Application No. 10-2021-0059537 filed on May 7, 2021, the entire contents of which are herein incorporated by reference.

TECHNICAL FIELD

The present disclosure relates to a method and a system for predicting a response to an immune checkpoint inhibitor, and more particularly, to a method and a system for generating a prediction result as to whether or not a patient associated with a pathology slide image responds to an immune checkpoint inhibitor, based on at least one of an immune phenotype of at least some regions in the pathology slide image or information associated with the immune phenotype.

BACKGROUND ART

Recently, a third-generation anticancer drug for cancer treatment, that is, an immune checkpoint inhibitor that utilize the immune system of the patient's body have gained attention. By the immune checkpoint inhibitor, it may refer to any drug that prevents cancer cells from evading the body's immune system or makes immune cells better recognize and attack cancer cells. Since it acts through the body's immune system, there are few side effects from the anticancer drugs, and the survival period of cancer patients treated with the immune checkpoint inhibitor may be longer than when treated with other anticancer drugs. However, these immune checkpoint inhibitor are not always effective for all cancer patients. Therefore, it is important to predict the response rate of the immune checkpoint inhibitor in order to predict the effect of the immune checkpoint inhibitor on the current cancer patient.

Meanwhile, the expression of PD-L1 may be used as a biomarker for predicting the response rate of the immune checkpoint inhibitor. That is, after obtaining tissue from the patient before treatment and staining it through the immunohistochemistry (IHC) method, an amount of expression of PD-L1 in the stained tissue is directly counted by a person, and it may then be predicted that the immune checkpoint inhibitor will be effective for patients with a certain expression or higher. According to this related technique, since a person directly calculates the PD-L1 expression by the eye, there is a problem in that such subjective factor can make it difficult to obtain objective quantification. In addition, since there are various factors to consider when predicting a response to the immune checkpoint inhibitor, prediction based on only one factor of PD-L1 expression can result in lowered accuracy. This is because, even in a situation in which PD-L1 is expressed, when immune cells are not present around cancer cells, it is difficult to show a response to the immune checkpoint inhibitor. In addition, it may be difficult to determine the shape of the spatial distribution of the immune cells associated with the antitumor effect of the immune checkpoint inhibitor only with the current method of quantifying the expression of PD-L1.

SUMMARY

Technical Problem

The present disclosure provides a method and a system for predicting a response to an immune checkpoint inhibitor to solve the problems described above.

Technical Solution

The present disclosure may be implemented in various ways, including a method, an apparatus (system), a computer readable storage medium storing instructions, or a computer program.

According to an embodiment of the present disclosure, a method, performed by at least one computing device, for predicting a response to an immune checkpoint inhibitor may include receiving a first pathology slide image, detecting one or more target items in the first pathology slide image, determining an immune phenotype of at least some regions in the first pathology slide image or information associated with the immune phenotype, based on a detection result for the one or more target items, and generating a prediction result as to whether or not a patient associated with the first pathology slide image responds to the immune checkpoint inhibitor, based on the immune phenotype of the at least some regions in the first pathology slide image or the information associated with the immune phenotype.

According to an embodiment, the detecting includes detecting the one or more target items in the first pathology slide image using an artificial neural network model for target item detection, and the artificial neural network model for target item detection is trained to detect one or more reference target items from a reference pathology slide image.

According to an embodiment, the at least some regions in the first pathology slide image include the one or more target items, the one or more target items include items associated with cancer and immune cells, and the determining includes calculating at least one of the number of, a distribution of, or a density of the immune cells in the items related to cancer in the at least some regions in the first pathology slide image, and determining at least one of an immune phenotype of at least some regions in the first pathology slide image or information associated with the immune phenotype, based on at least one of the calculated number, distribution, or density of the immune cells.

According to an embodiment, the items associated with cancer include a cancer area and a cancer stroma, and the calculating includes calculating a density of the immune cells in the cancer area in the at least some regions in the first pathology slide image, and calculating a density of the immune cells in the cancer stroma in the at least some regions in the first pathology slide image, and the determining includes based on at least one of the density of the immune cells in the cancer area or the density of the immune cells in the cancer stroma. determining at least one of the immune phenotype of the at least some regions in the first pathology slide image or the information associated with the immune phenotype.

According to an embodiment, if the density of the immune cells in the cancer area is equal to or greater than a first threshold density, the immune phenotype of the at least some regions in the first pathology slide image is determined to be immune inflamed, if the density of the immune cells in the cancer area is less than the first threshold density and the density of the immune cells in the cancer stroma is equal to or greater than a second threshold density, the immune phenotype of the at least some regions in the first pathology slide image is determined to be immune excluded, and if the density of the immune cells in the cancer area is less than the first threshold density and the density of the immune cells in the cancer stroma is less than the second threshold density, the immune phenotype of the at least some regions in the first pathology slide image is determined to be immune desert.

According to an embodiment, the first threshold density is determined based on a distribution of densities of the immune cells in the cancer area in each of a plurality of regions of interest in a plurality of pathology slide images, and the second threshold density is determined based on a distribution of densities of the immune cells in the cancer stroma in each of the plurality of regions of interest in the plurality of pathology slide images.

According to an embodiment, the determining includes, based on the number of the immune cells included in a specific region in the cancer area, determining the immune phenotype of the at least some regions in the first pathology slide image to be one of immune inflamed, immune excluded, or immune desert.

According to an embodiment, the determining includes determining the immune phenotype of the at least some regions in the first pathology slide image or the information associated with the immune phenotype by inputting a feature for each of the at least some regions in the first pathology slide image or the at least some regions in the first pathology slide image to an artificial neural network model for immune phenotype classification, and the artificial neural network model for immune phenotype classification is trained so as to, upon input of a feature for at least some regions in a reference pathology slide image or the at least some regions in the reference pathology slide image, determine at least one of an immune phenotype of the at least some regions in the reference pathology slide image or the information associated with the immune phenotype.

According to an embodiment, the feature for the at least some regions in the first pathology slide image includes at least one of: a statistical feature for the one or more target items in the at least some regions in the first pathology slide image; a geometric feature for the one or more target items; and an image feature corresponding to the at least some regions in the first pathology slide image.

According to an embodiment, the at least some regions in the first pathology slide image include a plurality of regions of interest, the immune phenotype of the at least some regions in the first pathology slide image includes an immune phenotype of each of the plurality of regions of interest, and the generating includes, based on the immune phenotype of each of the plurality of regions of interest, determining a most common immune phenotype included in the whole region of the first pathology slide image, and, based on the most common immune phenotype included in the whole region of the first pathology slide image, generating a prediction result as to whether or not the patient responds to the immune checkpoint inhibitor.

According to an embodiment, the generating includes, generating an immune phenotype map for the at least some regions in the first pathology slide image by using the immune phenotype of the at least some regions in the first pathology slide image, and inputting the generated immune phenotype map to a response prediction model for immune checkpoint inhibitor to generate a prediction result as to whether or not the patient responds to the immune checkpoint inhibitor, and the response prediction model for immune checkpoint inhibitor is trained to generate a reference prediction result upon input of a reference immune phenotype map.

According to an embodiment, the generating includes generating an immune phenotype feature map for the at least some regions in the first pathology slide image by using the information associated with the immune phenotype of the at least some regions in the first pathology slide image, and generating a prediction result as to whether or not the patient responds to the immune checkpoint inhibitor by inputting the generated immune phenotype feature map to a response prediction model for immune checkpoint inhibitor, and the response prediction model for immune checkpoint inhibitor is trained to generate a reference prediction result upon input of a reference immune phenotype feature map.

According to an embodiment, the method further includes obtaining information on expression of a biomarker from a second pathology slide image associated with the patient, in which the generating includes, based on at least one of the immune phenotype of the at least some regions in the first pathology slide image or the information associated with the immune phenotype, and the information on the expression of a biomarker, generating a prediction result as to whether or not the patient responds to the immune checkpoint inhibitor.

According to an embodiment, the biomarker is PD-L1, and the information on the expression of the PD-L1 includes at least one of a tumor proportion score (TPS) value or combined proportion score (CPS) value.

According to an embodiment, the biomarker is PD-L1, the obtaining includes receiving the second pathology slide image, and generating the information on the expression of the PD-L1 by inputting the second pathology slide image to an artificial neural network model for expression information generation, and the artificial neural network model for expression information generation is trained so as to, upon input of a reference pathology slide image, generate reference information on the expression of the PD-L1.

According to an embodiment, the generating the information on the expression of the PD-L1 by inputting the second pathology slide image to the artificial neural network model for expression information generation includes, generating the information on the expression of the PD-L1 by detecting, using the artificial neural network model for expression information generation, at least one of: a location of tumor cells; a location of lymphocytes; a location of macrophages; or whether or not PD-L1 is expressed, in at least some regions in the second pathology slide image.

According to an embodiment, the method further includes outputting at least one of: the detection result for the one or more target items; the immune phenotype of the at least some regions in the first pathology slide image; the information associated with the immune phenotype; the prediction result as to whether or not the patient responds to the immune checkpoint inhibitor; or the density of immune cells in the at least some regions in the first pathology slide image.

According to an embodiment, the method further includes, based on the prediction result as to whether or not the patient responds to a plurality of immune checkpoint inhibitors, outputting information on at least one immune checkpoint inhibitor suitable for the patient from among the plurality of immune checkpoint inhibitors.

There may be provided a computer program stored in a computer-readable recording medium for executing, on a computer, the method for predicting the response to the immune checkpoint inhibitor described above according to an embodiment of the present disclosure.

An information processing system according to an embodiment is provided, including a memory storing one or more instructions, and a processor configured to execute the stored one or more instructions to receive a first pathology slide image, detect one or more target items in the first pathology slide image, determine an immune phenotype of at least some regions in the first pathology slide image or information associated with the immune phenotype, based on a detection result for the one or more target items, and generate a prediction result as to whether or not a patient associated with the first pathology slide image responds to an immune checkpoint inhibitor, based on the immune phenotype of the at least some regions in the first pathology slide image or the information associated with the immune phenotype.

Advantageous Effects

According to some embodiments, it is possible to predict whether or not a patient will respond to an immune checkpoint inhibitor by using at least one of an immune phenotype determined from a pathology slide image or information associated with the immune phenotype. That is, by objectively analyzing the immune environment around the cancer cells, the predictive rate for whether or not a patient will respond to the immune checkpoint inhibitor can be improved.

According to some embodiments, it is possible to objectively quantify the expression of PD-L1 and predict whether or not a patient will respond to an immune checkpoint inhibitor using the quantified expression of PD-L1. By using the information on the expression of the PD-L1 as well as the immune phenotype determined from the pathology slide image and/or information associated with the immune phenotype together, the prediction accuracy of whether or not the patient will respond to the immune checkpoint inhibitor can be further increased.

According to some embodiments, using an artificial neural network model, it is possible to determine an immune phenotype and/or information associated with the immune phenotype or to obtain information on expression of PL-L1, thereby enabling more accurate and rapid processing than related art.

According to some embodiments, the user can visually and intuitively be provided with results generated in the process of predicting responsiveness to immune checkpoint inhibitor. In addition, the user may be provided with a report summarizing the results generated in the process of predicting responsiveness to the immune checkpoint inhibitor. Additionally, the user may receive recommendation on an immune checkpoint inhibitor and/or a combination of immune checkpoint inhibitors that is most suitable for a patient, among a plurality of immune checkpoint inhibitors, based on the results generated in the process of predicting responsiveness to the plurality of immune checkpoint inhibitors.

The effects of the present disclosure are not limited to the effects described above, and other effects not described will be able to be clearly understood by those of ordinary skill in the art (hereinafter, referred to as "those skilled in the art") from the description of the claims.

BRIEF DESCRIPTION OF THE DRAWINGS

Embodiments of the present disclosure will be described with reference to the accompanying drawings described below, in which like reference numerals denote like elements, but are not limited thereto.

FIGS. 11 to 15 are diagrams illustrating examples of outputting results generated in a process of predicting response or non-response to an immune checkpoint inhibitor according to another embodiment.

DETAILED DESCRIPTION OF THE INVENTION

Figure 1:
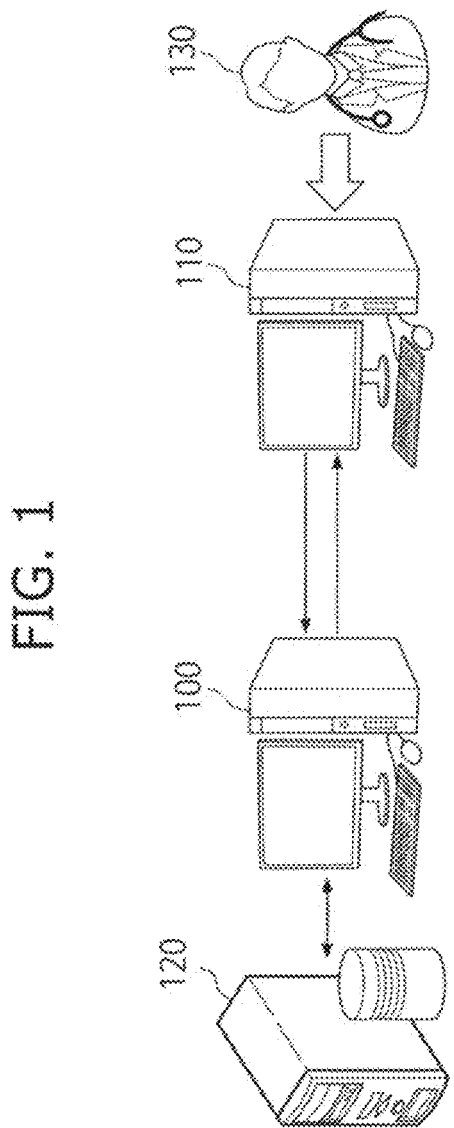
FIG. 1 is an exemplary configuration diagram illustrating a system in which an information processing system according to an embodiment of the present disclosure provides a prediction result of a response to an immune checkpoint inhibitor.

Hereinafter, specific details for the practice of the present disclosure will be described in detail with reference to the accompanying drawings. However, in the following description, detailed descriptions of well-known functions or configurations will be omitted when it may make the subject matter of the present disclosure rather unclear.

In the accompanying drawings, the same or corresponding elements are assigned the same reference numerals. In addition, in the following description of the embodiments, duplicate descriptions of the same or corresponding components may be omitted. However, even if descriptions of elements are omitted, it is not intended that such elements are not included in any embodiment.

Advantages and features of the disclosed embodiments and methods of accomplishing the same will be apparent by referring to embodiments described below in connection with the accompanying drawings. However, the present disclosure is not limited to the embodiments disclosed below, and may be implemented in various different forms, and the present embodiments are merely provided to make the present disclosure complete, and to fully disclose the scope of the invention to those skilled in the art to which the present disclosure pertains.

The terms used herein will be briefly described prior to describing the disclosed embodiments in detail. The terms used herein have been selected as general terms which are widely used at present in consideration of the functions of the present disclosure, and this may be altered according to the intent of an operator skilled in the art, conventional practice, or introduction of new technology. In addition, in a specific case, a term is arbitrarily selected by the applicant, and the meaning of the term will be described in detail in a corresponding description of the embodiments. Therefore, the terms used in the present disclosure should be defined based on the meaning of the terms and the overall contents of the present disclosure rather than a simple name of each of the terms.

As used herein, the singular forms "a," "an," and "the" are intended to include the plural forms as well, unless the context clearly indicates the singular forms. Further, the plural forms are intended to include the singular forms as well, unless the context clearly indicates the plural forms. As used throughout the description, when one part is referred to as "comprising" (or "including" or "having") other elements, the part can comprise (or include or have) only those elements or other elements as well as those elements unless specifically described otherwise.

Further, the term "module" or "unit" used herein refers to a software or hardware component, and "module" or "unit" performs certain roles. However, the meaning of the "module" or "unit" is not limited to software or hardware. The "module" or "unit" may be configured to be in an addressable storage medium or configured to reproduce one or more processors. Accordingly, as an example, the "module" or "unit" may include components such as software components, object-oriented software components, class components, and task components, and at least one of processes, functions, attributes, procedures, subroutines, program code segments of program code, drivers, firmware, micro-codes, circuits, data, database, data structures, tables, arrays, and variables. Furthermore, functions provided in the components and the "modules" or "units" may be combined into a smaller number of components and "modules" or "units", or further divided into additional components and "modules" or "units."

According to an embodiment, the "module" or "unit" may be implemented as a processor and a memory. The "processor" should be interpreted broadly to encompass a general-purpose processor, a central processing unit (CPU), a microprocessor, a digital signal processor (DSP), a controller, a microcontroller, a state machine, and so forth. Under some circumstances, the "processor" may refer to an application-specific integrated circuit (ASIC), a programmable logic device (PLD), a field-programmable gate array (FPGA), and so on. The "processor" may refer to a combination of processing devices, e.g., a combination of a DSP and a microprocessor, a plurality of microprocessors, one or more microprocessors in conjunction with a DSP core, or any other combination of such configurations. In addition, the "memory" should be interpreted broadly to encompass any electronic component capable of storing electronic information. The "memory" may refer to various types of processor-readable media such as random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or optical data storage, registers, and so on. The memory is said to be in electronic communication with a processor if the processor can read information from and/or write information to the memory. The memory integrated with a processor is in electronic communication with the processor.

In the present disclosure, the "system" may refer to at least one of a server device and a cloud device, but not limited thereto. For example, the system may include one or more server devices. As another example, the system may include one or more cloud devices. As another example, the system may be configured together with both a server device and a cloud device and operated.

In the present disclosure, "target data" may refer to any data or data item that can be used for training of a machine learning model, and may include, for example, data representing an image, data representing voice or voice characteristics, and the like, but is not limited thereto. In the present disclosure, the whole pathology slide image and/or at least one patch included in the pathology slide image are explained as the target data, but is not limited thereto, and any data that can be used for training a machine learning model may correspond to the target data. In addition, the target data may be tagged with label information through an annotation task.

In the present disclosure, the "pathology slide image" refers to an image obtained by capturing a pathological slide fixed and stained through a series of chemical treatments in order to observe a tissue removed from a human body with a microscope. For example, the pathology slide image may refer to a digital image captured with a microscope, and may include information on cells, tissues, and/or structures in the human body. In addition, the pathology slide image may include one or more patches, and the one or more patches may be tagged with label information (e.g., information on immune phenotype) through the annotation work. For example, the "pathology slide image" may include H&E-stained tissue slides and/or IHC-stained tissue slides, but is not limited thereto, and tissue slides applied with various staining methods (e.g., chromogenic in situ hybridization (CISH), Fluorescent in situ hybridization (FISH), Multiplex IHC, and the like), or unstained tissue slides may also be included. As another example, the "pathology slide image" may be a patient's tissue slide generated to predict a response to an immune checkpoint inhibitor, and it may include a tissue slide of a patient before treatment with the immune checkpoint inhibitor and/or a tissue slide of a patient after treatment with the immune checkpoint inhibitor.

In the present disclosure, the "patch" may refer to a small region within the pathology slide image. For example, the patch may include a region corresponding to a semantic object extracted by performing segmentation on the pathology slide image. As another example, the patch may refer to a combination of pixels associated with the label information generated by analyzing the pathology slide image.

In the present disclosure, "at least some regions in the pathology slide image" may refer to at least some regions in the pathology slide image to be analyzed. For example, the at least some regions in the pathology slide image may refer to at least some regions in the pathology slide image that include a target item. As another example, the at least some regions in the pathology slide image may refer to at least some of a plurality of patches generated by segmenting the pathology slide image. In addition, the "at least some regions in the pathology slide image" may refer to all or a part of all regions (or all patches) forming the pathology slide image. In the present disclosure, the "at least some regions in the pathology slide image" may be referred to as a region of interest, and conversely, the region of interest may refer to at least some regions in the pathology slide image.

In the present disclosure, a "machine learning model" and/or an "artificial neural network model" may include any model that is used for inferring an answer to a given input. According to an embodiment, the machine learning model may include an artificial neural network model including an input layer (layer), a plurality of hidden layers, and output layers. In an example, each layer may include a plurality of nodes. For example, the machine learning model may be trained to infer label information for pathology slide images and/or at least one patch included in the pathology slides. In this case, the label information generated through the annotation task may be used to train the machine learning model. In addition, the machine learning model may include weights associated with a plurality of nodes included in the machine learning model. In an example, the weight may include an any parameter associated with the machine learning model.

In the present disclosure, "training" may refer to any process of changing a weight associated with the machine learning model using at least one patch and the label information. According to an embodiment, the training may refer to a process of changing or updating weights associated with the machine learning model through one or more of forward propagation and backward propagation of the machine learning model using at least one patch and the label information.

In the present disclosure, the "label information" is correct answer information of the data sample information, which is acquired as a result of the annotation task. The label or label information may be used interchangeably with terms such as annotation, tag, and so on as used in the art. In the present disclosure, the "annotation" may refer to an annotation work and/or annotation information (e.g., label information, and the like) determined by performing the annotation work. In the present disclosure, the "annotation information" may refer to information for the annotation work and/or information generated by the annotation work (e.g., label information).

In the present disclosure, the "target item" may refer to data/information, an image region, an object, and the like to be detected in the pathology slide image. According to an embodiment, the target item may include a target to be detected from the pathology slide image for diagnosis, treatment, prevention, or the like of a disease (e.g., cancer). For example, the "target item" may include a target item in units of cells and a target item in units of areas.

In the present disclosure, an "immune phenotype of at least some regions of the pathology slide" may be determined based on at least one of the number, distribution, and density of immune cells in the at least some regions of the pathology slide. Such an immune phenotype may be expressed in various classification schemes, and for example, the immune phenotype may be represented as immune inflamed, immune excluded, or immune desert.

In the present disclosure, "information associated with immune phenotype" may include any information representing or characterizing an immune phenotype. According to an embodiment, the information associated with immune phenotype may include a feature value of the immune phenotype. In this example, the feature value of the immune phenotype may include various vectors related to the immune phenotype, such as a score value (score or density value for each class of the classifier) corresponding to the class corresponding to the immune phenotype (e.g., immune inflamed, immune excluded, and immune desert) and/or a feature fed as an input to the classifier, and the like. For example, information associated with immune phenotype may include: 1) score values associated with immune phenotype output from an artificial neural network or a machine learning model; 2) density value, number, various statistics, or vector value expressing the distribution of immune cells, and the like of immune cells applied to a threshold (or cut-off) for the immune phenotype; 3) scalar value, vector value, or the like that includes the relative relationship (e.g., histogram vector or graph expression vector considering the direction and distance) or relative statistics (e.g., ratio of the number of immune cells to the number of other cells and the like) for immune cells or cancer cells and other cell types (cancer cells, immune cells, fibroblasts, lymphocytes, plasma cells, macrophage, endothelial cells, and the like), and the like; and 4) scalar values or vector values including statistics (e.g., ratio of the number of immune cells to the cancer stroma region, and the like) or distributions (e.g., histogram vectors or graph expression vectors, and the like) for immune cells and cancer cells and adjacent regions (e.g., cancer area, cancer stroma region, tertiary lymphoid structure, normal area, necrosis, fat, blood vessel, high endothelial venule, lymphatic vessel, nerve, and the like), and the like.

In the present disclosure, "each of a plurality of A" and/or "respective ones of a plurality of A" may refer to each of all components included in the plurality of A, or may refer to each of some of the components included in a plurality of A. For example, each of the plurality of regions of interests may refer to each of all regions of interests included in the plurality of regions of interests or may refer to each of some regions of interests included in the plurality of regions of interests.

In the present disclosure, "instructions" may refer to one or more instructions grouped based on functions, which are the components of a computer program and executed by the processor.

In the present disclosure, a "user" may refer to a person who uses a user terminal. For example, the user may include an annotator who performs an annotation work. As another example, the user may include a doctor, a patient, and the like provided with a prediction result of a response to an immune checkpoint inhibitor (e.g., a prediction result as to whether or not the patient responds to an immune checkpoint inhibitor). In addition, the user may refer to the user terminal, or conversely, the user terminal may refer to the user. That is, the user and the user terminal may be interchangeably used herein.

FIG. 1 is an exemplary configuration diagram illustrating a system in which an information processing system 100 according to an embodiment of the present disclosure provides a prediction result of a response to an immune checkpoint inhibitor. As illustrated, the system for providing a prediction result of a response to an immune checkpoint inhibitor (e.g., a prediction result as to whether or not a patient responds to an immune checkpoint inhibitor) may include the information processing system 100, a user terminal 110, and a storage system 120. In an example, the information processing system 100 may be configured to be connected to each of the user terminal 110 and the storage system 120 for communication. While FIG. 1 illustrates one user terminal 110, the present disclosure is not limited thereto, and in an exemplary configuration, a plurality of user terminals 110 may be connected to the information processing system 100 for communication. In addition, while the information processing system 100 is shown as one computing device in FIG. 1, embodiment is not limited thereto, and the information processing system 100 may be configured to process information and/or data in a distributed manner through a plurality of computing devices. In addition, while the storage system 120 is shown as a single device in FIG. 1, embodiment is not limited thereto, and the system may be configured with a plurality of storage devices or as a system that supports a cloud. In addition, respective components of the system for providing a prediction result of a response to the immune checkpoint inhibitor illustrated in FIG. 1 represent functional components that can be divided on the basis of functions, and in an actual physical environment, a plurality of components may be implemented as being incorporated with each other.

The information processing system 100 and the user terminal 110 are any computing devices used to generate and provide a prediction result of a response to the immune checkpoint inhibitor. In an example, the computing device may refer to any type of device equipped with a computing function, and may be a notebook, a desktop, a laptop, a server, a cloud system, and the like, for example, but is not limited thereto.

The information processing system 100 may receive a first pathology slide image. For example, the information processing system 100 may receive the first pathology slide image from the storage system 120. As another example, the information processing system 100 may receive the first pathology slide image from the user terminal 110. The information processing system 100 may be configured to generate, through the received first pathology slide image, a prediction result as to whether or not the patient associated with the first pathology slide image responds to the immune checkpoint inhibitor.

In an embodiment, the information processing system 100 may detect one or more target items in the first pathology slide image. For example, the information processing system 100 may detect one or more target items in the first pathology slide image by using an artificial neural network model for target item detection. In this example, the artificial neural network model for target item detection may correspond to a model trained to detect one or more reference target items from the reference pathology slide image. In this example, the one or more target items may include items associated with cancer and immune cells. In addition, the item associated with cancer may include a cancer area and a cancer stroma. In the present specification, the cancer area may be used interchangeably with cancer epithelium.

Based on the detection result for one or more target items, the information processing system 100 may determine at least one of an immune phenotype of at least some regions in the pathology slide image or information associated with the immune phenotype. In an embodiment, the information processing system 100 may calculate at least one of the number of, a distribution of, or a density of the immune cells in the items related to cancer in at least some regions in the pathology slide image, and based on at least one of the calculated number, distribution, or density of the immune cells, determine at least one of an immune phenotype of at least some regions in the pathology slide image or information associated with the immune phenotype. For example, the information processing system 100 may calculate a density of immune cells in the cancer area and a density of immune cells in the cancer stroma in at least some regions in the pathology slide image, and based on at least one of the density of the immune cells in the cancer area or the density of the immune cells in the cancer stroma, determine at least one of an immune phenotype of at least some regions in the pathology slide image or information associated with the immune phenotype.

In this case, if the density of the immune cells in the cancer area is equal to or greater than a first threshold density, the immune phenotype of at least some regions in the pathology slide image may be determined to be immune inflamed. In addition, if the density of the immune cells in the cancer area is less than the first threshold density and the density of the immune cells in the cancer stroma is equal to or greater than a second threshold density, the immune phenotype of at least some regions in the pathology slide image may be determined to be immune excluded. In addition, if the density of the immune cells in the cancer area is less than the first threshold density and the density of the immune cells in the cancer stroma is less than the second threshold density, the immune phenotype of at least some regions in the pathology slide image may be determined to be immune desert. In this example, the first threshold density may be determined based on a distribution of the density of the immune cells in the cancer area in each of a plurality of regions of interest in the plurality of pathology slide images, and the second threshold density may be determined based on a distribution of the density of the immune cells in the cancer stroma in each of a plurality of regions of interest in the plurality of pathology slide images. Additionally or alternatively, the information processing system 100 may determine the immune phenotype of one or more regions of interest to be one of immune inflamed, immune excluded, or immune desert based on the number of immune cells included in a specific region in the cancer area.

In another embodiment, the information processing system 100 may input a feature for at least some regions in the pathology slide image or the at least some regions in the pathology slide image to an artificial neural network model for immune phenotype classification, thereby determining at least one of an immune phenotype of at least some regions in the pathology slide image or information associated with the immune phenotype. In this example, the artificial neural network model for immune phenotype classification may correspond to a model that is trained to determine at least one of an immune phenotype of at least some regions in the pathology slide image or information associated with the immune phenotype, upon input of the feature for at least some regions in the reference pathology slide image or the at least some regions in the reference pathology slide image. In this example, the feature for at least some regions in the pathology slide image may include at least one of: a statistical feature for one or more target items in at least some regions in the pathology slide image; a geometric feature for one or more target items; or an image feature corresponding to at least some regions in the pathology slide image. In addition, at least some regions in the pathology slide image input to the artificial neural network model for immune phenotype classification may include: at least some regions in H&E-stained images; at least some regions in IHC-stained images; at least some regions in multiplex IHC-stained images, and the like, but is not limited thereto.

The information processing system 100 may generate a prediction result as to whether or not a patient associated with the first pathology slide image responds to the immune checkpoint inhibitor, based on at least one of the immune phenotype of at least some regions in the pathology slide image or the information associated with the immune phenotype. In an embodiment, based on the immune phenotype of each of the plurality of regions of interest of the first pathology slide image, the information processing system 100 may determine the most common immune phenotype (that is, a representative immune phenotype) included in the whole region of the first pathology slide image. Based on the most common immune phenotype included in the whole region of the first pathology slide image determined as described above, the information processing system 100 may generate a prediction result as to whether or not the patient responds to the immune checkpoint inhibitor.

In another embodiment, the information processing system 100 may use the immune phenotype of at least some regions in the pathology slide image to generate an immune phenotype map for at least some regions in the pathology slide image, and input the generated immune phenotype map to a response prediction model for immune checkpoint inhibitor, to generate a prediction result as to whether or not the patient responds to the immune checkpoint inhibitor. In this example, the response prediction model for immune checkpoint inhibitor may include a statistical model and/or an artificial neural network model trained to generate a reference prediction result upon input of the reference immune phenotype map.

In still another embodiment, the information processing system 100 may obtain information on expression of a biomarker from a second pathology slide image associated with the patient, and generate a prediction result as to whether or not the patient responds to the immune checkpoint inhibitor based on at least one of an immune phenotype of at least some regions in the first pathology slide image and information associated with the immune phenotype, and the information on the expression of the biomarker. In this example, the biomarker may be PD-L1, but is not limited thereto, and may include CD3, CD8, CD68, FOXP3, CD20, CD4, CD45, CD163, and other various biomarkers related to immune cells. In this example, the information on the expression of the PD-L1 may include at least one of a tumor proportion score (TPS) and a combined proportion score (CPS). For example, the information processing system 100 may receive the second pathology slide image and input the second pathology slide image to an artificial neural network model for expression information generation to generate information on the expression of the biomarker. For example, the information processing system 100 may use the artificial neural network model for expression information generation to detect at least one of location of cells (tumor cells, lymphocytes, macrophages, and the like) present in at least some regions in the second pathology slide image, whether or not the cells express biomarkers, the number of positive cells of the biomarker, and a score for an amount of the positive cells of the biomarker, thereby generating information on the expression of the biomarker. In this example, the artificial neural network model for expression information generation may correspond to a model trained to generate reference information on the expression of the biomarker upon input of the reference pathology slide image.

For example, the information processing system 100 may receive the second pathology slide image and input the second pathology slide image to the artificial neural network model for expression information generation to generate information on the expression of PD-L1. For example, the information processing system 100 may use the artificial neural network model for expression information generation to detect at least one of location of tumor cells, location of lymphocytes, location of macrophages, or whether or not PD-L1 is expressed, in at least some regions in the second pathology slide image, to generate the information on the expression of the PD-L1. In this example, the artificial neural network model for expression information generation may correspond to a model trained to generate reference information on the expression of PD-L1 upon input of the reference pathology slide image.

The information processing system 100 may output, through the user terminal 110, at least one of a detection result for the one or more target items, an immune phenotype of at least some regions in the pathology slide image, information associated with the immune phenotype, a prediction result as to whether or not the patient responds to the immune checkpoint inhibitor, or a density of immune cells in each of at least some regions in the pathology slide image. That is, the user 130 (e.g., a doctor, a patient, and the like) may receive results generated in the process of predicting a response to the immune checkpoint inhibitor through the user terminal 110. Additionally or alternatively, the information processing system 100 may output, through the user terminal 110, information on at least one immune checkpoint inhibitor suitable for the patient, among a plurality of immune checkpoint inhibitors, based on the prediction result as to whether or not the patient responds to the immune checkpoint inhibitors.

The storage system 120 is a device or a cloud system that stores and manages pathology slide images associated with a target patient and various data associated with a machine learning model to provide a prediction result of a response to an immune checkpoint inhibitor. For efficient data management, the storage system 120 may store and manage various types of data using a database. In this example, the various data may include any data associated with the machine learning model, and include, for example, a file of the target data, meta information of the target data, label information for the target data that is the result of the annotation work, data related to the annotation work, a machine learning model (e.g., an artificial neural network model), and the like, but are not limited thereto. While FIG. 1 shows the information processing system 100 and the storage system 120 as separate systems, embodiment is not limited thereto, and they may be incorporated into one system.

Since information on the overall distribution of immune cells (e.g., how much immune cells are infiltrating into cancer cells, and the like) plays an important role in predicting the response to an immune checkpoint inhibitor, when predicting the response to the immune checkpoint inhibitor, information on the various distribution of immune cells in H&E-stained pathology slide images (that is, H&E-stained tissue slide images) may be used. According to some embodiments of the present disclosure, by objectively analyzing the immune environment around cancer cells, it is possible to increase the predictive rate of whether or not a patient will respond to the immune checkpoint inhibitor. In addition, it is possible to objectively quantify the expression of PD-L1 and predict whether or not a patient will respond to the immune checkpoint inhibitor by using the quantified expression of PD-L1.

Figure 2:
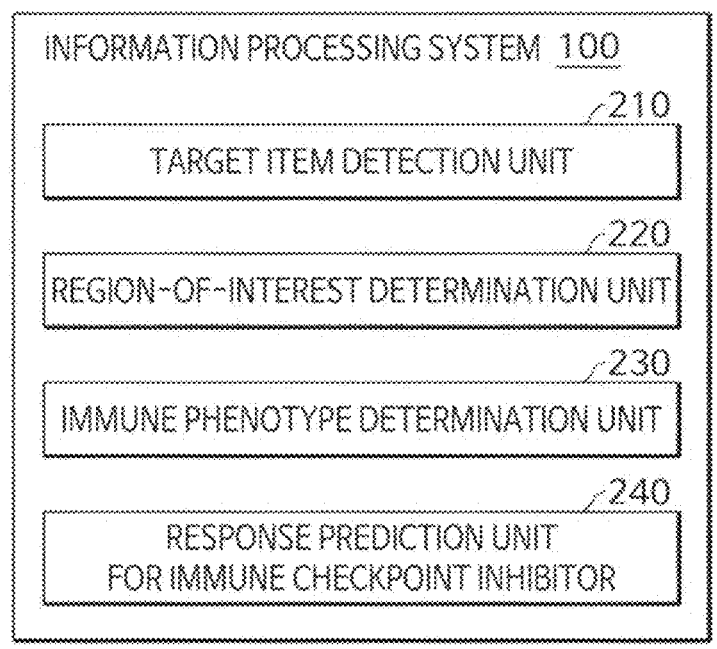
FIG. 2 is a block diagram illustrating an internal configuration of the information processing system according to an embodiment.

FIG. 2 is a block diagram illustrating an internal configuration of the information processing system 100 according to an embodiment. According to an embodiment, as illustrated, the information processing system 100 may include a target item detection unit 210, a region-of-interest determination unit 220, an immune phenotype determination unit 230, and a response prediction unit 240 for to immune checkpoint inhibitor. Respective components of the information processing system 100 illustrated in FIG. 2 represent functional components that can be divided on the basis of functions, and in an actual physical environment, a plurality of components may be implemented as being incorporated with each other.

The target item detection unit 210 may receive the pathology slide image (e.g., H&E-stained first pathology slide image, IHC-stained second pathology slide image, and the like), and detect one or more target items in the received first pathology slide image. In an embodiment, the target item detection unit 210 may use the artificial neural network model for target item detection to detect one or more target items in the first pathology slide image. For example, the target item detection unit 210 may detect tumor cell, lymphocyte, macrophages, dendritic cell, fibroblast, endothelial cell, blood vessel, cancer stroma, cancer epithelium, cancer area, normal area (e.g., normal lymph node architecture region), and the like, as the target item in the first pathology slide image.

The region-of-interest determination unit 220 may determine one or more regions of interest in the first pathology slide image. In this example, the region of interest may include a region in which one or more target items are detected in the pathology slide image. For example, the region-of-interest determination unit 220 may determine, as the region of interest, a patch including one or more target items from among a plurality of patches forming the first pathology slide image. In the present disclosure, it is illustrated that the region-of-interest determination unit 220 is included in the information processing system 100, but embodiments are not limited thereto, and the information processing system 100 may process at least some regions in the first pathology slide image by the immune phenotype determination unit 230 and the response prediction unit 240 for immune checkpoint inhibitor without determining a region of interest.

The immune phenotype determination unit 230 may determine at least one of the immune phenotype of at least some regions (e.g., one or more regions of interest, and the like) in the first pathology slide image or the information associated with the immune phenotype, based on the detection result for the one or more target items. In an embodiment, the immune phenotype determination unit 230 may calculate at least one of the number of, a distribution of, or a density of the immune cells in the items related to cancer in at least some regions in the first pathology slide image, and based on at least one of the calculated number, distribution, or density of the immune cells, determine at least one of the immune phenotype of at least some regions in the first pathology slide image or the information associated with the immune phenotype. For example, the immune phenotype determination unit 230 may calculate at least one of a density of immune cells in the cancer area or a density of immune cells in the cancer stroma in one or more regions of interest, and based on the calculated result, determine the immune phenotype of one or more regions of interest and/or the information associated with the immune phenotype. Additionally, the immune phenotype determination unit 230 may determine the immune phenotype of one or more regions of interest to be one of immune inflamed, immune excluded, or immune desert, based on the number of immune cells included in the specific region in the cancer area.

In an embodiment, the immune phenotype determination unit 230 may input at least one of a feature for at least some regions in the first pathology slide image, or the at least some regions in the first pathology slide image to the artificial neural network model for immune phenotype classification, to determine the immune phenotype of the at least some regions in the first pathology slide image or the information associated with the immune phenotype. In this example, the feature for at least some regions in the first pathology slide image may include at least one of: a statistical feature for one or more target items in at least some regions in the first pathology slide image; a geometric feature for one or more target items; or an image feature corresponding to at least some regions in the first pathology slide image. Additionally or alternatively, the feature for at least some regions in the first pathology slide image may include a feature merging two or more of the statistical feature, the geometric feature, and the image feature described above.

The response prediction unit 240 for immune checkpoint inhibitor may generate a prediction result as to whether or not a patient associated with the first pathology slide image responds to an immune checkpoint inhibitor, based on the immune phenotype of at least some regions in the first pathology slide image and/or the information associated with the immune phenotype.

In an embodiment, the response prediction unit 240 for immune checkpoint inhibitor may, based on the immune phenotype of each of the plurality of regions of interest of the first pathology slide image, determine the most common immune phenotype included in the whole region of the first pathology slide image, and based on the most common immune phenotype included in the whole region of the first pathology slide image, generate a prediction result as to whether or not the patient responds to the immune checkpoint inhibitor. In another embodiment, the response prediction unit 240 for immune checkpoint inhibitor may generate an immune phenotype map for at least some regions in the first pathology slide image by using the immune phenotype of at least some regions in the first pathology slide image, and input the generated immune phenotype map to a response prediction model for immune checkpoint inhibitor, to generate a prediction result as to whether or not the patient responds to the immune checkpoint inhibitor.

In this example, the immune phenotype map may refer to a set of regions of interest generated as at least some regions in the first pathology slide image are classified into one of three immune phenotypes. For example, the immune phenotype map may refer to a map in which the immune phenotype of each of a plurality of regions of interest is indicated on a pathology slide image. Additionally or alternatively, the immune phenotype map may include an immune phenotype feature map that may further include information associated with the three immune phenotypes (e.g., a score for immune phenotype output from the artificial neural network model for immune phenotype classification, a density value of immune cells applied to a threshold (or cut-off) for the immune phenotype, and the like).

In still another embodiment, the response prediction unit 240 for immune checkpoint inhibitor may obtain information on expression of a biomarker (e.g., PD-L1, and the like) from the second pathology slide image (e.g., an IHC-stained pathology slide image of the region corresponding to the first pathology slide image) associated with the patient. In this case, the response prediction unit 240 for immune checkpoint inhibitor may generate a prediction result as to whether or not the patient responds to the immune checkpoint inhibitor based on at least one of an immune phenotype of at least some regions in the first pathology slide image or information associated with the immune phenotype, and the information on the expression of the biomarker. In this example, the information on the expression of the biomarker may be generated by inputting the second pathology slide image to the artificial neural network model for expression information generation.

In FIG. 2, the information processing system 100 includes the target item detection unit 210, the region-of-interest determination unit 220, the immune phenotype determination unit 230, and the response prediction unit 240 for immune checkpoint inhibitor, but is not limited thereto. and some components may be omitted or other components may be added. In an embodiment, the information processing system 100 may further include an output unit (not illustrated), and the output unit may output at least one of a detection result for the one or more target items, an immune phenotype of at least some regions in the first pathology slide image, information associated with the immune phenotype, a prediction result as to whether or not the patient responds to the immune checkpoint inhibitor, or a density of immune cells in each of one or more regions of interest. For example, the output unit may output information on at least one immune checkpoint inhibitor suitable for the patient from among a plurality of immune checkpoint inhibitors.

Figure 3:
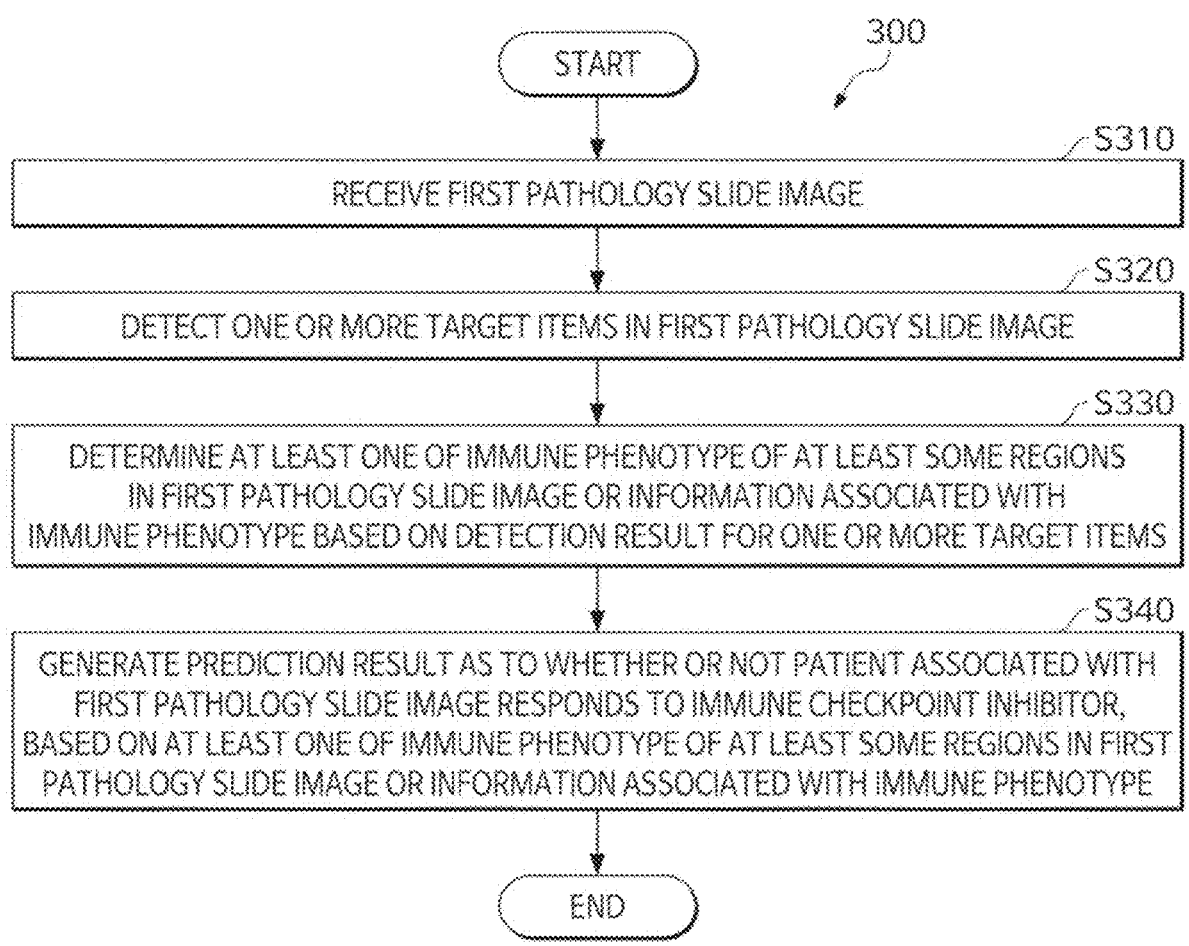
FIG. 3 is a flowchart illustrating a method for predicting a response to an immune checkpoint inhibitor according to an embodiment.

FIG. 3 is a flowchart illustrating a method 300 for predicting a response to an immune checkpoint inhibitor according to an embodiment. In an embodiment, the method 300 for predicting a response to the immune checkpoint inhibitor may be performed by a processor (e.g., by at least one processor of an information processing system). The method 300 for predicting a response to an immune checkpoint inhibitor may be initiated by the processor receiving a first pathology slide image (S310). The processor may detect one or more target items in the first pathology slide image (S320). For example, the processor may detect one or more target items in the first pathology slide image by using an artificial neural network model for target item detection.

Then, based on the detection result for the one or more target items, the processor may determine at least one of an immune phenotype of at least some regions in the first pathology slide image or information associated with the immune phenotype (S330). In this example, the at least some regions in the first pathology slide image may include one or more target items, and the one or more target items may include items associated with cancer and immune cells. For example, the processor may calculate at least one of the number of, a distribution of, or a density of the immune cells in the items related to cancer in at least some regions in the first pathology slide image, and based on at least one of the calculated number, distribution, and/or density of the immune cells, determine an immune phenotype of at least some regions in the first pathology slide image and/or information associated with the immune phenotype.

The processor may generate a prediction result as to whether or not the patient associated with the first pathology slide image responds to the immune checkpoint inhibitor, based on at least one of the immune phenotype of at least some regions in the pathology slide image or the information associated with the immune phenotype (S340). In an embodiment, based on the most common immune phenotype included in the whole region of the first pathology slide image, the processor may generate a prediction result as to whether or not the patient responds to an immune checkpoint inhibitor. In another embodiment, the processor may generate the prediction result as to whether or not the patient responds to an immune checkpoint inhibitor, by inputting the immune phenotype map for at least some regions in the first pathology slide image into a response prediction model for immune checkpoint inhibitor. In still another embodiment, the processor may generate an immune phenotype feature map for at least some regions in the first pathology slide image by using the information associated with the immune phenotype of the at least some regions in the first pathology slide image, and input the generated immune phenotype feature map to the response prediction model for immune checkpoint inhibitor to generate a prediction result as to whether or not the patient responds to immune checkpoint inhibitor.

In still another embodiment, the processor may obtain information on expression of a biomarker from a second pathology slide image associated with the patient, and generate a prediction result as to whether or not the patient responds to an immune checkpoint inhibitor based on an immune phenotype of at least some regions in the first pathology slide image and the information on the expression of the biomarker. To this end, the processor may receive the second pathology slide image associated with the patient, and input the second pathology slide image to the artificial neural network model for expression information generation to generate information on the expression of the biomarker. In this example, the second pathology slide image may correspond to a pathology slide image of a region corresponding to the first pathology slide image.

Figure 4:
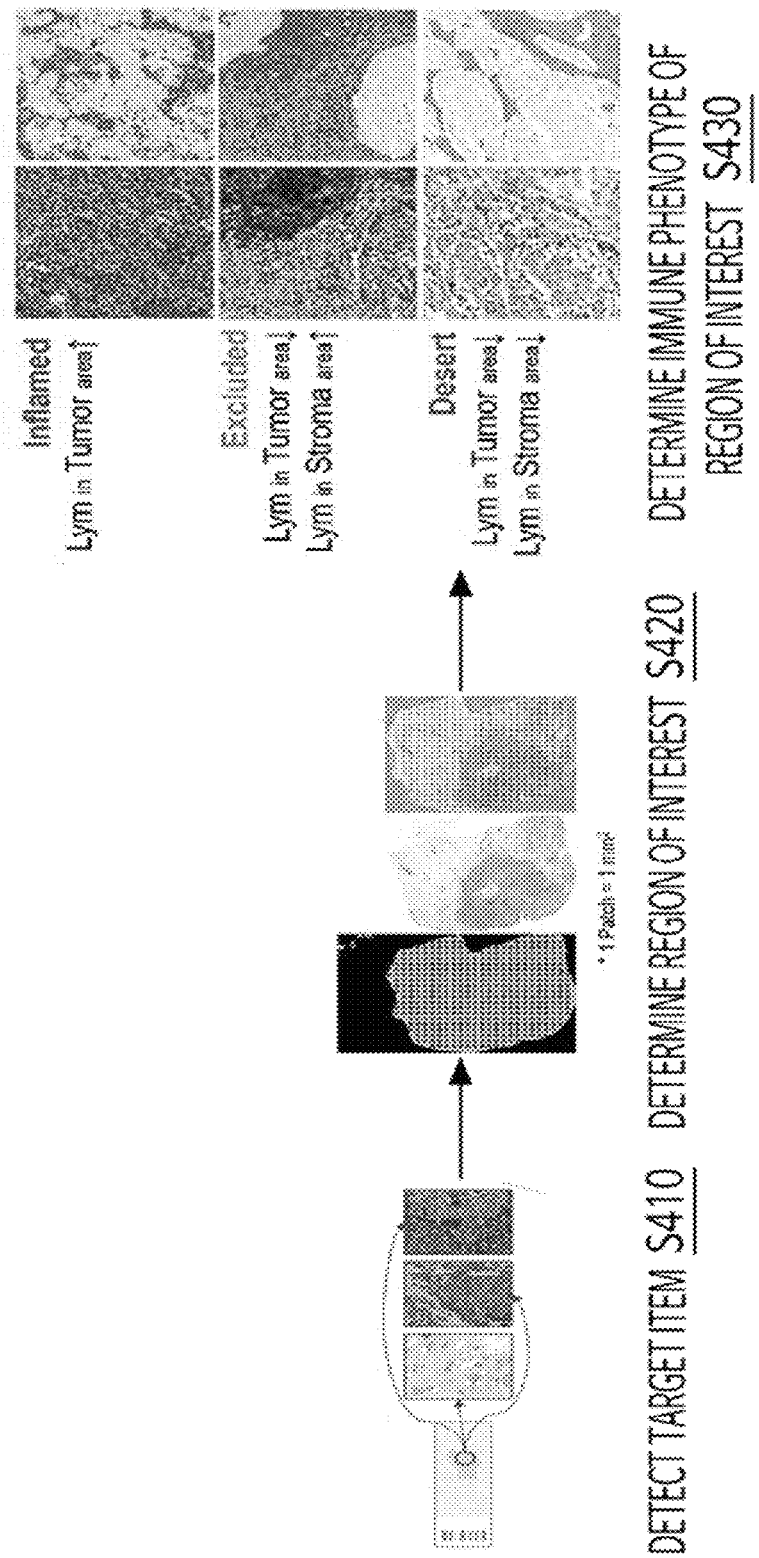
FIG. 4 is a diagram illustrating an example of detecting a target item in a pathology slide image, determining a region of interest, and determining an immune phenotype of the region of interest according to an embodiment.

FIG. 4 is a diagram illustrating an example of detecting a target item in a pathology slide image, determining a region of interest, and determining an immune phenotype of the region of interest according to an embodiment. In order to predict whether or not a patient will respond to an immune checkpoint inhibitor, a user (e.g., a doctor, a researcher, and the like) may obtain a patient's tissue (e.g., tissue immediately before treatment, and the like) and generate one or more pathology slide images. For example, the user may perform H&E staining on the obtained patient's tissue, and digitize the H&E-stained tissue slide through a scanner to generate a pathology slide image (e.g., the first pathology slide image). As another example, the user may perform IHC staining on the obtained patient's tissue, and digitize the IHC-stained tissue slide through a scanner to generate a pathology slide image (e.g., the second pathology slide image).

The processor (e.g., at least one processor of the information processing system) may use an artificial neural network model for target item detection to detect various target items from the pathology slide image (e.g., the digitized H&E tissue images (whole slide image)) (S410). In this example the artificial neural network model for target item detection may correspond to a model trained to detect one or more reference target items from the reference pathology slide image. For example, the processor may detect a tumor cell, a lymphocyte, a macrophage, a dendritic cell, a fibroblast, an endothelial cell, and the like, as a target item in units of cells. Additionally or alternatively, the processor may detect a cancer stroma, a cancer epithelium, a cancer area, a normal area (e.g., region including normal lymph node architecture) and the like, as a target item in units of areas.

In an embodiment, the processor may use an artificial neural network model trained to detect the target item in units of cells, to detect the target item in units of cells in the pathology slide image. Additionally or alternatively, the processor may use the artificial neural network model trained to detect the target item in units of areas, to detect the target item in units of areas in the pathology slide image. That is, the artificial neural network model that detects the target item in units of cells and the artificial neural network model that detects the target item in units of areas may be the separate models from each other. In contrast, the processor may use the artificial neural network model trained to detect both the target item in units of cells and the target item in units of areas at the same time, to detect the target item in units of cells and/or the target item in units of areas in the pathology slide image. That is, using one artificial neural network model, it is possible to detect both the target item in units of cells and the target items in units of areas.

The result of detecting the target item in units of cells and the result of detecting the target item in units of areas may be complementary to each other. In an embodiment, the processor may estimate a cancer area (that is, a detection result for target item in units of areas) in the pathology slide image, based on a detection result for the tumor cells (that is, the detection result for the target item in units of cells), or modify or change the estimated cancer area. Conversely, the processor may estimate a tumor cell (that is, a detection result for target item in units of cells) in the pathology slide image through the detection result for the cancer area (that is, the detection result for target item in units of areas), or modify or change the estimated tumor cell. That is, while there is a difference that the cancer area corresponds to the target item in units of areas and the tumor cell corresponds to the target item in units of cells, since the region including tumor cells eventually corresponds to the cancer area, the detection result for target item in units of cells and the detection result for target item in units of areas may be complementary to each other.

For example, when detecting a target item in units of areas, a detection error may occur, such as omission of detection of a target item (that is, tumor cells) in units of cells at a sub level and the like, and the processor may supplement the detection result according to whether or not the cells in the region detected as the cancer area are actually detected as tumor cells. In addition, conversely, the detection result may be supplemented according to whether or not the region detected as a tumor cell is detected as a cancer area. As described above, the processor may use the detection result for the target item in units of cells and the detection result for the target item in units of areas to supplement each other's strengths and weaknesses, and may minimize errors in the detection result.

The processor may detect items associated with cancer and immune cells, including a cancer area (e.g., cancer epithelium), cancer stroma and/or tumor cells in the pathology slide image (e.g., entire H&E-stained slide image) (S410). Then, the processor may determine one or more regions of interest in the pathology slide image (S420). For example, the processor may determine that at least some patches (e.g., patches in which items associated with cancer and immune cells are detected) from among a plurality of patches (e.g., patches of size 1 mm2) generated by dividing the pathology slide image into N grids (where N is any natural number) are the region of interest (e.g., at least some regions in the pathology slide image).

The processor may determine an immune phenotype of one or more regions of interest based on the detection result for the items associated with cancer and immune cells in the one or more regions of interest (S430). In this example, the one or more regions of interest may include a plurality of pixels, and the detection result for the items and/or immune cells associated with cancer in the one or more regions of interest may include predictive values for each of the items associated with cancer and immune cells in each of the plurality of pixels included in the one or more regions of interest. In an embodiment, the processor may calculate at least one of the number of, a distribution of, or a density of immune cells in the item associated with cancer in the one or more regions of interest, and determine the immune phenotype of the one or more regions of interest based on at least one of the calculated number, distribution, or density of immune cells. For example, the processor may calculate, in one or more regions of interest, a density of immune cells in the cancer area (lymphocyte in tumor region) and a density of immune cells in the cancer stroma (lymphocyte in stroma region), and determine the immune phenotype of the one or more regions of interest based on at least one of the density of immune cells in the cancer area or the density of immune cells in the cancer stroma. Additionally, the processor may determine the immune phenotype of one or more regions of interest to be one of immune inflamed, immune excluded, or immune desert, with reference to the number of immune cells included in a specific region in the cancer area.

As illustrated in FIG. 4, if the density of the immune cells in the cancer area is equal to or greater than a first threshold density, the immune phenotype of one or more regions of interest may be determined to be immune inflamed. In addition, if the density of the immune cells in the cancer area is less than the first threshold density and the density of the immune cells in the cancer stroma is equal to or greater than a second threshold density, the immune phenotype of one or more regions of interest may be determined to be immune excluded. In addition, if the density of the immune cells in the cancer area is less than the first threshold density and the density of the immune cells in the cancer stroma is less than the second threshold density, the immune phenotype of one or more regions of interest may be determined to be immune desert.

In this example, the first threshold density may be determined based on a distribution of the density of the immune cells in the cancer area in each of a plurality of regions of interest in the plurality of pathology slide images. Likewise, the second threshold density may be determined based on a distribution of the density of the immune cells in the cancer stroma in each of the plurality of regions of interest in the plurality of pathology slide images. For example, the first threshold density may correspond to a density value corresponding to top X % (where X is a number between 0 and 100) in the distribution for the density of immune cells in the cancer area in each of the regions of interest of the plurality of pathology slide images. Likewise, the second threshold density may correspond to a density value corresponding to the top Y % (where Y is a number between 0 and 100) in the distribution for the density for immune cells within the cancer stroma in each of the regions of interest of the plurality of pathology slide images. The values of X and/or Y may be determined on a biological basis according to the related art or on any basis.

The first threshold density and the second threshold density may be the same as or different from each other. In addition, each of the first threshold density or the second threshold density may include two or more threshold densities. In an embodiment, the first threshold density or the second threshold density may include a threshold density for an upper area and a threshold density for a lower area. For example, when the density of immune cells in the cancer area is equal to or greater than the threshold density of the upper area among the first threshold densities, it may correspond to when the density of immune cells in the cancer area is equal to or greater than the first threshold density. In addition, when the density of immune cells in the cancer area is less than the threshold density for the lower area among the first threshold densities, it may correspond to when the density of immune cells in the cancer area is less than the first threshold density.

FIG. 4 illustrates generating a determination (S430) of an immune phenotype of the region of interest, but embodiments are not limited thereto, and information associated with the immune phenotype may be generated. In order to generate the information associated with the immune phenotype, the processor may use the factors described above, which are used in determining the immune phenotype, or the like. For example, such factors may include at least one of the number of, a distribution of, or a density of immune cells in an item associated with cancer, and the like.

Figure 5:
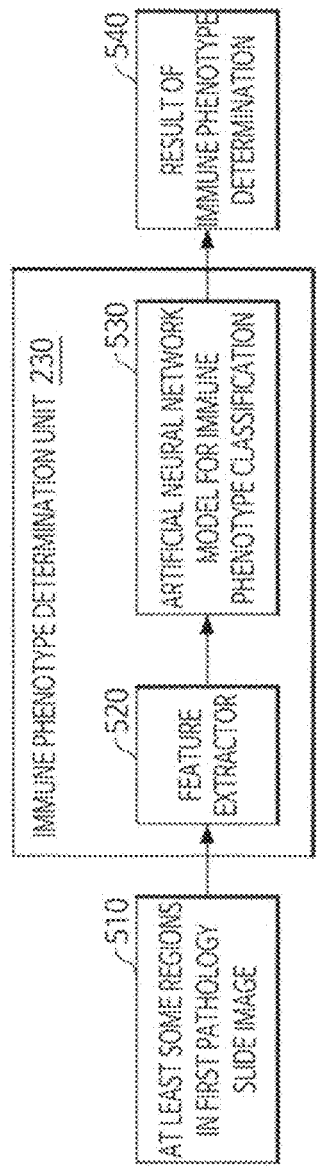
FIG. 5 is a diagram illustrating an example of generating an immune phenotype determination result according to an embodiment.

FIG. 5 is a diagram illustrating an example of generating an immune phenotype determination result 540 according to an embodiment. In an embodiment, the processor (e.g., at least one processor of the information processing system) may input the feature for at least some regions in the first pathology slide image into the artificial neural network model 530 for immune phenotype classification to determine the immune phenotype of at least some regions in the first pathology slide image. In this example, the artificial neural network model 530 for immune phenotype classification may correspond to a classifier that is trained to determine the immune phenotype of at least some regions in the reference pathology slide image to be one of immune inflamed, immune excluded, or immune desert, upon input of the feature for at least some regions in the reference pathology slide image.

In this example, the feature for at least some regions in the first pathology slide image may include a statistical feature for one or more target items of at least some regions in the first pathology slide image (e.g., a density of, the number of, and the like of a specific target item in at least some regions in the first pathology slide image), a geometric feature for one or more target items (e.g., a feature including relative position information between specific target items, and the like), and/or an image feature corresponding to at least some regions in the first pathology slide image (e.g., a feature extracted from a plurality of pixels included in at least some regions in the first pathology slide image, an image vector corresponding to at least some regions in the first pathology slide image, and the like), and the like. Additionally or alternatively, the feature for at least some regions in the first pathology slide image may include a feature obtained by concatenating two or more features among the statistical feature for the one or more target items in the at least some regions in the first pathology slide image, the geometric feature for the one or more target items, and the image feature corresponding to the at least some regions in the first pathology slide image.

The immune phenotype determination unit 230 of the information processing system may receive at least some regions 510 in the first pathology slide image and determine the immune phenotype of the at least some regions 510 in the first pathology slide image. In this example, the at least some regions 510 in the first pathology slide image input to the immune phenotype determination unit 230 may include a detection result for a target item in the at least some regions 510 in the first pathology slide image. As illustrated, a feature extraction unit 520 of the immune phenotype determination unit 230 may receive the at least some regions 510 in the first pathology slide image, extract the feature for each of the at least some regions 510 in the first pathology slide image, and input the result to the artificial neural network model 530 for immune phenotype classification. Accordingly, the artificial neural network model 530 for immune phenotype classification may determine the immune phenotype of each of the at least some regions 510 in the first pathology slide image, and output the immune phenotype determination result 540.

FIG. 5 illustrates that the feature extractor unit 520 is included in the immune phenotype determination unit 230, and the immune phenotype determination unit 230 receives the at least some regions 510 in the first pathology slide image, but embodiments are not limited thereto. For example, the immune phenotype determination unit 230 may receive the feature itself, of each of the at least some regions 510 in the first pathology slide image, and input it to the artificial neural network model 530 for immune phenotype classification and output the immune phenotype determination result 540.

FIG. 5 illustrates that the artificial neural network model 530 for immune phenotype classification receives the feature for at least some regions in the first pathology slide image, but embodiments are not limited thereto, and it may be configured to receive and process at least some regions in the first pathology slide image. Additionally or alternatively, the artificial neural network model 530 for immune phenotype classification may be configured to output not only the immune phenotype determination result 540, but also at least one of information associated with the immune phenotype. In this case, the artificial neural network model 530 for immune phenotype classification may be trained to determine at least one of the immune phenotype of at least some regions in the reference pathology slide image or the information associated with the immune phenotype, upon input of the feature for the at least some regions in the reference pathology slide image or the at least some regions in the reference pathology slide image.

Figure 6:
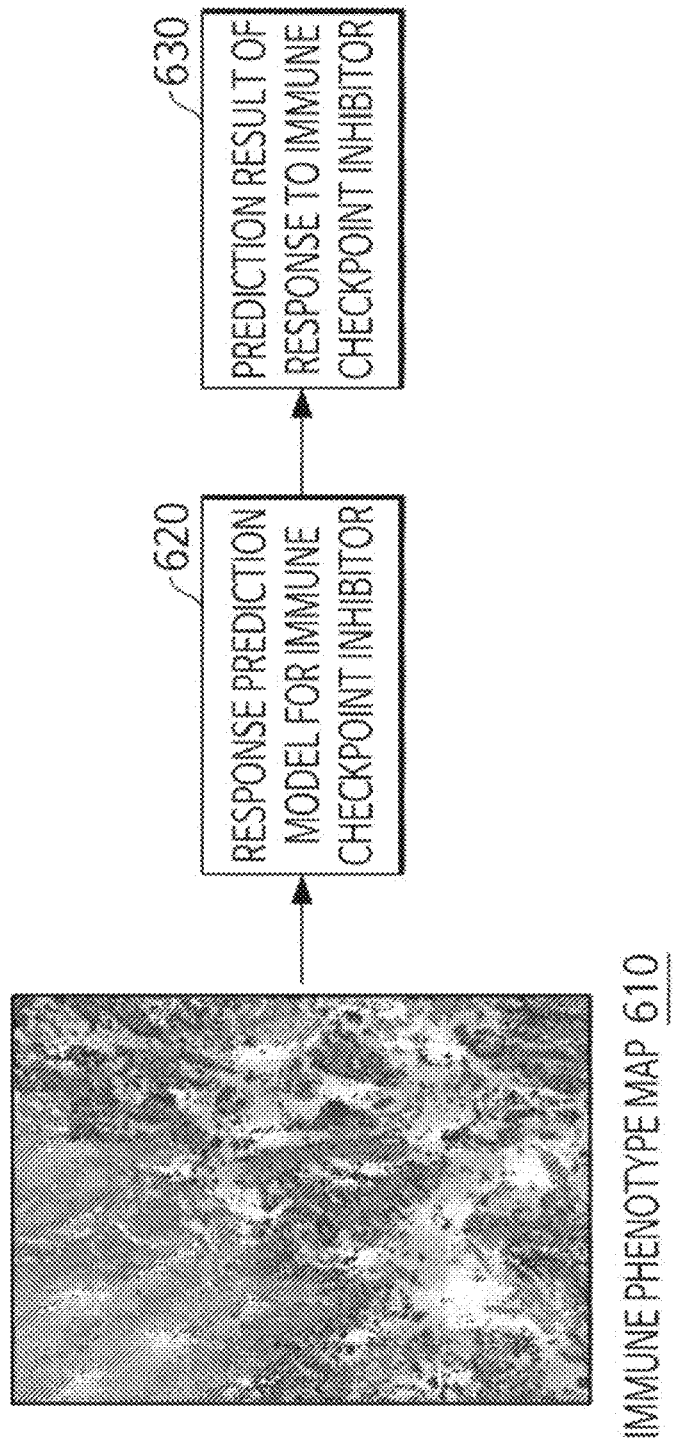
FIG. 6 is a diagram illustrating an example of generating a prediction result of a response to an immune checkpoint inhibitor according to an embodiment.

FIG. 6 is a diagram illustrating an example of generating a prediction result 630 of a response to an immune checkpoint inhibitor according to an embodiment. The processor may determine the immune phenotype for each of the plurality of regions of interest in the pathology slide image (e.g., in the first pathology slide image). Then, the processor may generate a prediction result as to whether or not the patient associated with the pathology slide image responds to an immune checkpoint inhibitor, based on the immune phenotype of each of the plurality of regions of interest (that is, the immune phenotype for each of the plurality of regions of interest). For example, the processor may generate a prediction result as to whether or not the patient associated with the pathology slide image will respond to the immune checkpoint inhibitor, based on the distribution of immune phenotypes in the pathology slide image.

In an embodiment, the processor may determine the most common immune phenotype included in the whole region of the pathology slide image, based on the immune phenotype of each of the plurality of regions of interest. Then, the processor may generate a prediction result as to whether or not the patient will respond to the immune checkpoint inhibitor, based on the most common immune phenotype included in the whole region of the pathology slide image. For example, if the most common immune phenotype included in the whole region of the pathology slide image is immune inflamed, the processor may predict that the patient associated with that pathology slide image will respond to the immune checkpoint inhibitor (that is, the patient is a responder). In contrast, if the most common immune phenotype included in the whole region of the pathology slide image is immune excluded or immune desert, the processor may predict that the patient associated with that pathology slide image will not respond to the immune checkpoint inhibitor (that is, the patient is a non-responder).

In another embodiment, the processor may use the immune phenotype of the at least some regions in the first pathology slide image to generate an immune phenotype map 610 for at least some regions in the first pathology slide image. For example, the processor may generate the immune phenotype map as a set that is generated by classifying the plurality of regions of interest based on the immune phenotype of at least some regions (e.g., each of the plurality of regions of interest) in the first pathology slide image. In this example, the immune phenotype map may include an immune phenotype feature map, and the immune phenotype feature map may further include not only the immune phenotype of the region of interest, but also information associated with the same. For example, the processor may generate an immune phenotype feature map including information on an immune phenotype of at least some regions in the first pathology slide image, a score for each immune phenotype (e.g., a score output from the artificial neural network model for immune phenotype classification, and the like), and the number of, a distribution of, or a density of immune cells in an item associated with cancer (e.g., a density of immune cells in the cancer area or the density of immune cells in the cancer stroma, and the like).

Then, as illustrated, the processor may input the generated immune phenotype map 610 to a response prediction model 620 for immune checkpoint inhibitor to generate a prediction result 630 as to whether or not the patient responds to the immune checkpoint inhibitor. For example, the processor may input the immune phenotype map 610 to the response prediction model 620 for immune checkpoint inhibitor to classify the patient associated with the corresponding pathology slide image into responder or non-responder. In this case, the response prediction model 620 for immune checkpoint inhibitor may take into consideration the spatial information and/or location information or the like between immune phenotypes to finally predict the patient's response rate. For example, the response prediction model 620 for immune checkpoint inhibitor may collect at least one or more global features for the pathology slide image based on the immune phenotype map. To this end, the response prediction model 620 for immune checkpoint inhibitor may be configured to form a graph, or use various pooling methods (e.g., RNN, CNN, simple average pooling, sum pooling, max pooling, bag-of-words/VLAD/Fisher, and the like) based on the immune phenotype map.

In this example, the response prediction model 620 for immune checkpoint inhibitor may correspond to a statistical model and/or an artificial neural network model trained to generate a prediction result as to response or non-response to a reference immune checkpoint inhibitor upon input of a reference immune phenotype map. For example, a user (e.g., a doctor, or the like) may perform an annotation work based on actual treatment results of a plurality of patients, to determine a label as a responder or a non-responder for each patient's pathology slide image. Then, the processor may train the response prediction model 620 for immune checkpoint inhibitor by using the pathology slide image (or the immune phenotype map for the pathology slide image of each patient) and the label of each patient. As another example, upon input of the graph of the immune phenotype, the processor may train the response prediction model 620 for immune checkpoint inhibitor to classify it into responder or non-responder. To this end, the processor may generate, by transform, a graph of the immune phenotype that represents or characterizes the immune phenotype corresponding to the region of interest in the immune phenotype map.

In another embodiment, the processor may generate an immune phenotype feature map for at least some regions in the first pathology slide image by using the information associated with the immune phenotype of the at least some regions in the first pathology slide image. Then, the processor may input the generated immune phenotype feature map to the response prediction model 620 for immune checkpoint inhibitor, to generate a prediction result as to whether or not the patient responds to the immune checkpoint inhibitor. In this case, the response prediction model 620 for immune checkpoint inhibitor may be trained to generate a reference prediction result upon input of the reference immune phenotype feature map.

Figure 7:
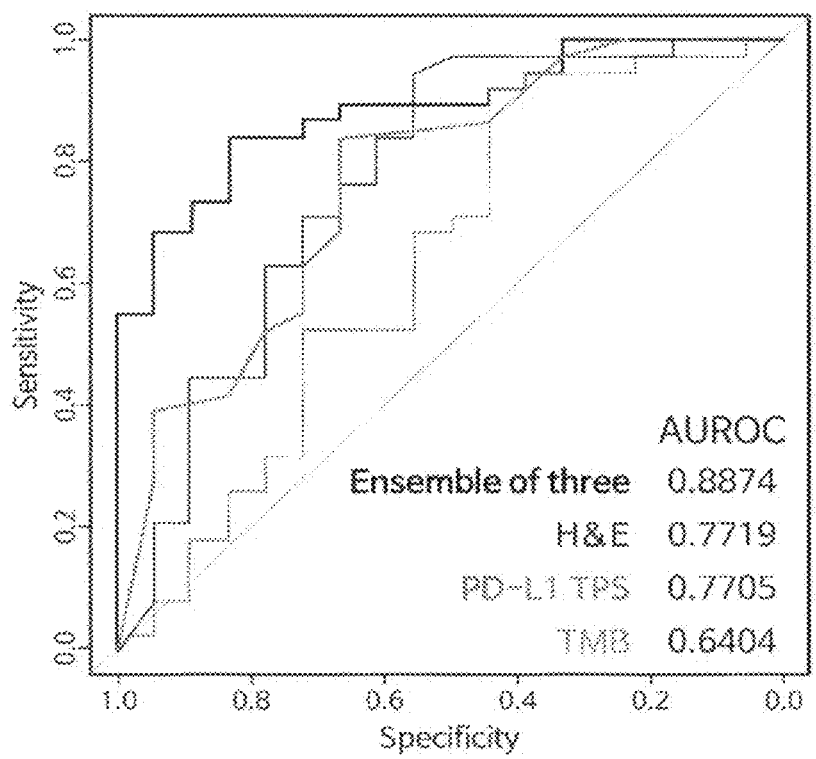
FIG. 7 is a view illustrating a result of analyzing the predictive performance of information on expression of PD-L1 and/or immune phenotype information on response or non-response to an immune checkpoint inhibitor according to an embodiment.

FIG. 7 is a view illustrating a result of analyzing the predictive performance of information on expression of a biomarker and/or immune phenotype information on response or non-response to an immune checkpoint inhibitor according to an embodiment. The processor (e.g., at least one processor of an information processing system) may obtain information on expression of a biomarker (e.g., PD-L1) from a pathology slide image associated with the patient (e.g., a second pathology slide image corresponding to the first pathology slide image). In this case, the processor may generate a prediction result as to whether or not the patient responds to the immune checkpoint inhibitor, based on the information on the immune phenotype and the PD-L1 expression of at least some regions in the first pathology slide image. In this example, the information on the expression of the PD-L1 may include at least one of a tumor proportion score (TPS) and a combined proportion score (CPS). Furthermore, the processor may obtain additional patient data, such as a patient's tumor mutation burden (TMB) value, microsatellite instability (MSI) value, homologous recombination deficiency (HRD) value, and the like, to predict whether or not the patient will respond to the immune checkpoint inhibitor.

In an embodiment, the processor may receive a second pathology slide image (e.g., an IHC-stained pathology slide image), and input the second pathology slide image to the artificial neural network model for expression information generation to generate information on PD-L1 expression. For example, the processor may use the artificial neural network model for expression information generation to detect at least one of a location of a tumor cell, a location of a lymphocyte, a location of a macrophage, or whether or not PD-L1 is expressed in at least some regions in the first pathology slide image included in the second pathology slide image, to thus generate information on the PD-L1 expression. In this example, the artificial neural network model for expression information generation may correspond to a model trained to generate reference information on the expression of PD-L1 upon input of the reference pathology slide image. In another embodiment, the processor may receive information on PD-L1 expression directly calculated by a user (e.g., a pathologist) from a pathology slide image (e.g., an IHC-stained pathology slide image).

For example, among the information on PD-L1 expression, TPS may be calculated according to Equation 1 below.

$$TPS = \frac{N \text{ of } PD-L1 \text{ positive tumor cells}}{N \text{ of viable tumor cells}} \times 100(\%) \quad \langle\text{Equation 1}\rangle$$

The patient may be classified into one or more groups based on the calculated TPS value and the cut-off value of the TPS. For example, for non-small cell lung cancer, if TPS<1%, the patient may be classified as "group without PD-L1 expression", and if 1%≤TPS≤49%, the patient may be classified as "group with PD-L1 expression", and if TPS≥50%, the patient may be classified as a "group with high PD-L1 expression". The cut-off value of TPS is not limited to the values (1%, 49%, 50%) described above, and may vary according to the type of cancer, the type of the PD-L1 antibody, and the like.

As another example, CPS among the information on PD-L1 expression may be calculated according to Equation 2 below. In this case, the maximum upper limit of the CPS may be 100, and if the CPS calculated according to Equation 2 is greater than 100, the CPS may be determined as 100.

$$CPS = \frac{N \text{ of } PD-L1 \text{ positive tumor cells, lymphocyte, macrophage}}{N \text{ of viable tumor cells}} \times 100 \quad \langle\text{Equation 2}\rangle$$

The patient may be classified into one or more groups based on the calculated CPS value and the cut-off value of the CPS. For example, by setting 10% as the cut-off value of CPS, patients may be classified into a group having CPS≥10% or a group having CPS<10%, but embodiments are not limited thereto, and the cut-off value of CPS may vary according to the type of cancer, the type of the PD-L1 antibody, and the like.

Table 710 illustrated in the drawing shows that, as a result of comparing a patient with the immune phenotype (that is, with the representative immune phenotype) classified as the immune inflamed ("inflamed" in Table 710) and a patient with immune phenotype not classified as immune inflamed ("not-inflamed" in Table 710), based on response or non-response to the immune checkpoint inhibitor, the overall response rate (ORR) and the median progression-free survival (mPFS) were improved in group of patients with PD-L1 TPS of 1% to 49% and group of patients with 50% or more. Therefore, the processor may generate a meaningful prediction result with respect to whether or not a patient will respond to the immune checkpoint inhibitor by using the information on the immune phenotype and PD-L1 expression together. In table 710, N denotes the number of patients, CI denotes confidence interval, HR denotes hazard ratio, and HR denotes not reached.

In addition, regarding the prediction of response or non-response to the immune checkpoint inhibitor (that is, whether or not a patient responds to the immune checkpoint inhibitor), the graph 720 illustrated in the drawing shows the receiver operating characteristic (ROC) curves for specificity-sensitivity in the examples of using the TPS of PD-L1 (that is, "PD-L1 TPS"), using the immune phenotype (that is, "H&E"), using TMB (that is, "TMB"), and using all of the information described above (that is, "Ensemble of three"), respectively. According to the graph 720 illustrated, Area Unser ROC curve (AUROC) of TMB is calculated as 0.6404, AUROC of PD-L1 TPS is calculated as 0.7705, AUROC of H&E is calculated as 0.7719, and AUROC of Ensemble of three is calculated as 0.8874. In other words, it has been proven that the best performance is when predicting response or non-response to the immune checkpoint inhibitor using both the information on the expression of the PD-L1 (that is, PD-L1 TPS and TMB) and the immune phenotype (that is, H&E).

Figure 8:
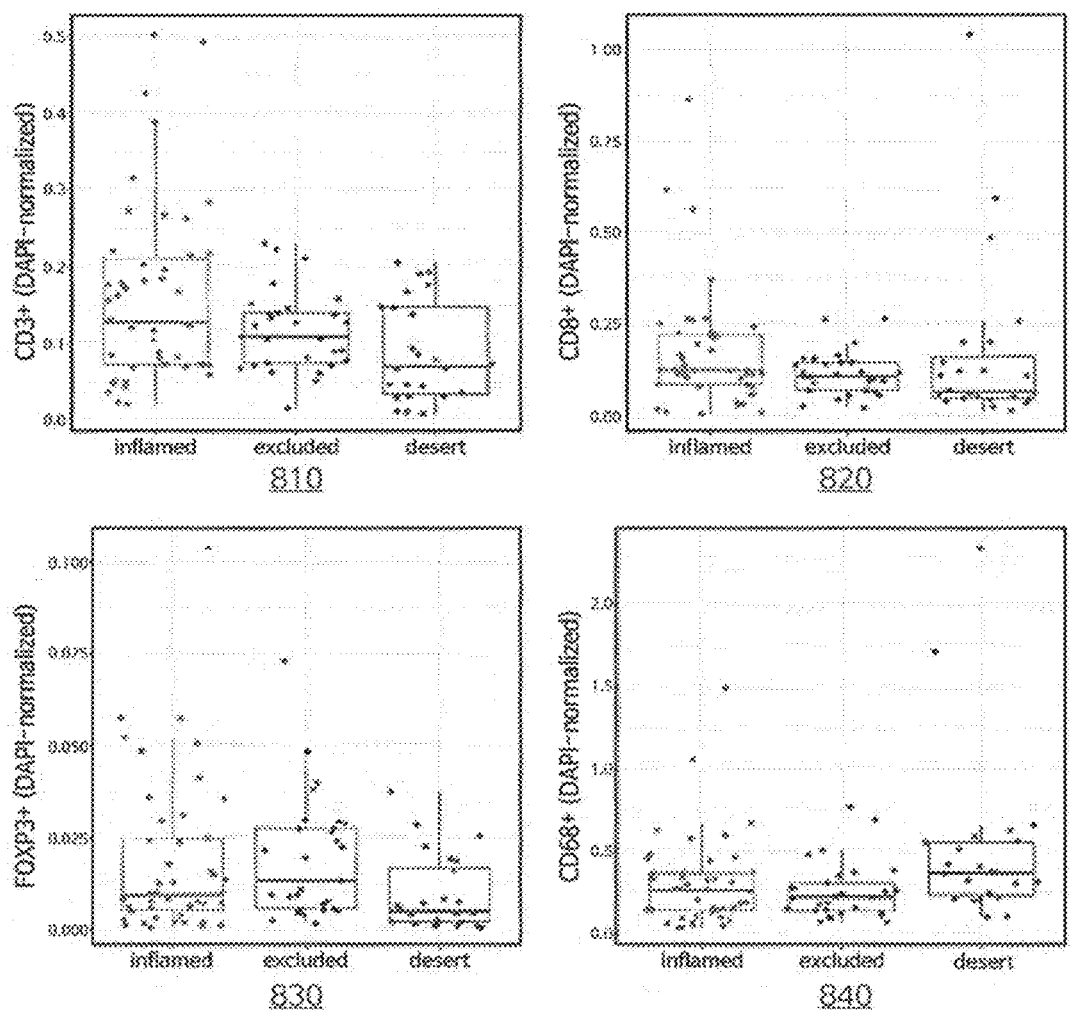
FIG. 8 is a graph illustrating the correlation between immune phenotype and information on the expression of CD3-positive cells, CD8-positive cells, FOXP3-positive cells, and CD68-positive cells according to an embodiment.

FIG. 8 is a graph illustrating the correlation between immune phenotype and information on the expression of CD3-positive cells, CD8-positive cells, FOXP3-positive cells, and CD68-positive cells according to an embodiment. The processor (e.g., at least one processor of the information processing system) may calculate an inflamed score (IS) based on the immune phenotype of each of the plurality of regions of interest in the pathology slide image. In this example, the inflamed score may be defined as a ratio of a region of interest (e.g., a region of size 1 mm2 that makes up the pathology slide image) among a plurality of regions of interest in the pathology slide image, which has been determined to be the immune phenotype of immune inflamed and which includes a tumor. For example, the inflamed score may be calculated by Equation 3 below.

$$\text{Inflamed Score} = \frac{N \text{ of the inflamed grids}}{(N \text{ of inflamed+excluded+desert grids})} \quad \langle\text{Equation 3}\rangle$$

In this example, N of inflamed+excluded+desert grids denotes the number of a plurality of regions of interest in the pathology slide image, and N of the inflamed grids denotes the number of regions of interest with the immune phenotype corresponding to immune inflamed.

With the cut-off value of the activity score as 20%, as a result of comparing the overall survival period of patients (N (number of patients)=1,013) after treatment with the immune checkpoint inhibitor for 10 types of cancers, it has been proven that patients with inflamed scores above the cut-off value have a longer overall survival period after treatment with the immune checkpoint inhibitor for melanoma and head and neck cancer as well as lung cancer. In addition, even when lung cancer was included (N=519) or excluded (N=494), it was observed that patients with higher inflamed scores tended to have a better prognosis for treatment with the immune checkpoint inhibitor.

In this experiment, for pathological validation of immune phenotype, a H&E-stained pathology slide image of a patient were segmented into multiple patches of 1 mm2, and the immune phenotype was determined based on the tumor-infiltrating lymphocyte (TIL) in the cancer area and the TIL in the cancer stroma in each patch. Based on the immune phenotype of each of the plurality of patches in the pathology slide image, a representative immune phenotype (that is, the immune phenotype with the most common portion in the pathology slide image) was determined. For example, if the inflamed score is 33.3% or more, the representative immune phenotype of the corresponding pathology slide image may be determined to be immune inflamed.

Next, multiplex IHC staining was performed on non-small cell lung cancer (NSCLC) tissues treated with the immune checkpoint inhibitor to perform staining for biomarkers CD3, CD8, CD20, CD68, FOXP3, CK, and DAPI. The number of normalized cells may be calculated by dividing the total number of positive cells by the number of DAPI-positive cells in the pathology slide image. For example, the normalized number of CD3-positive cells may be calculated based on Equation 4 below.

$$\text{Normalized } CD3 \mathrel{+}= \frac{N \text{ of } CD3-\text{positive cells}}{N \text{ of } DAPI \text{ cells}} \quad \text{(Equation 4)}$$

where, Normalized ED 3 denotes the number of normalized CD3-positive cells, N of CD3-positive cells denotes the number of CD3-positive cells, and N of DAPI cells denotes the number of DAPI cells.

The graphs 810, 820, 830 and 840 illustrated in the drawing shows the correlation between the immune phenotype (that is, representative immune phenotype) determined from the H&E-stained pathology slide image as described above and the expression of the biomarker identified through multiplex IHC analysis. According to the first graph 810 and the second graph 820, the normalized CD3-positive cells and CD8-positive cells, which play an anti-tumor activity role, appeared more greatly in the pathology slide image corresponding to immune inflamed compared to the other immune phenotypes (CD3, FC (fold change)=1.57, P=0.0182) (CD8, FC=1.24, P=0.0697).

On the other hand, according to the third graph 830, the FOXP3-positive cells associated with immunosuppressive activity appeared greatly in the pathology slide image corresponding to immune excluded (FC=1.26, P=0.0656). In addition, according to the fourth graph 840, the CD68-positive cells appeared greatly in the pathology slide image corresponding to the immune desert (FC 1.76, P=0.00467). Accordingly, the processor may generate a meaningful prediction result as to whether or not the patient responds to the immune checkpoint inhibitor based on the immune phenotype determined from the H&E-stained pathology slide image.

Figure 9:
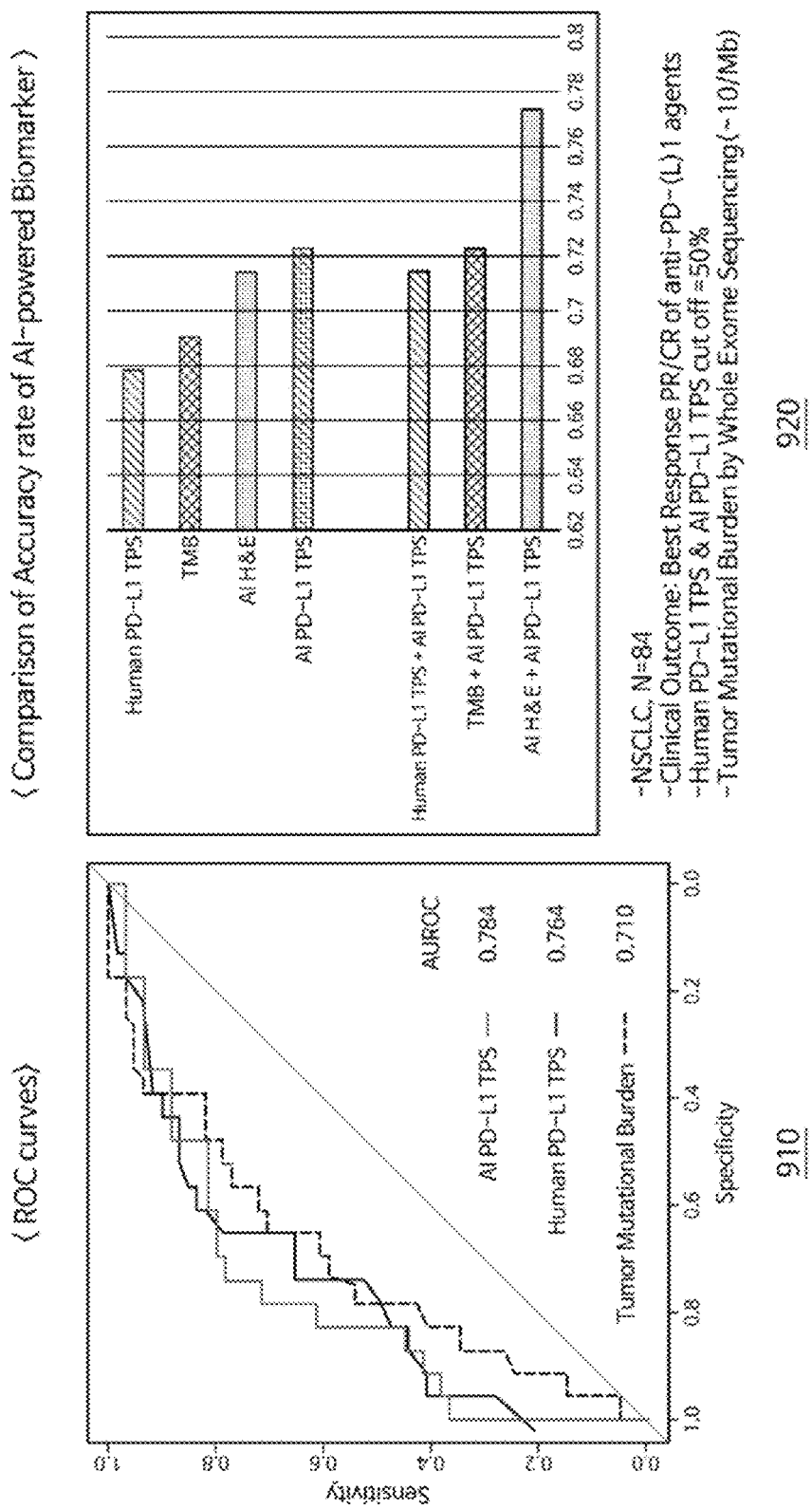
FIG. 9 are graphs showing the performance of various methods for predicting whether or not a patient responds to an immune checkpoint inhibitor according to an embodiment.

FIG. 9 are graphs 910 and 920 showing the performance of various methods for predicting whether or not a patient responds to an immune checkpoint inhibitor according to an embodiment. In order to generate a prediction result as to whether or not the patient responds to the immune checkpoint inhibitor, the processor (e.g., at least one processor of the information processing system) may determine the immune phenotype for the patient's first pathology slide image (e.g., H&E-stained pathology slide image) according to the embodiments described above. In this example, the immune phenotype for the pathology slide image may refer to the immune phenotype of one or more regions of interest in the pathology slide image, the most common immune phenotype included in the pathology slide image (that is, the representative immune phenotype), the immune phenotype map, and the like.

Additionally or alternatively, in order to generate a prediction result as to whether or not the patient responds to the immune checkpoint inhibitor, the processor may obtain information on the PD-L1 expression (e.g., TPS, CPS) from a second pathology slide image (e.g., IHC-stained pathology slide image) associated with the patient. For example, the information on PD-L1 expression may correspond to information directly calculated by a user. As another example, the information on PD-L1 expression may correspond to information generated by the processor from the second pathology slide image of the patient using the artificial neural network model for expression information generation.

In an embodiment, the processor may receive the second pathology slide image and input the second pathology slide image to the artificial neural network model for expression information generation to generate the information on PD-L1 expression. Additionally or alternatively, the processor may use the artificial neural network model for expression information generation to detect at least one of a location of a tumor cell, a location of a lymphocyte, a location of a macrophage, or whether or not PD-L1 is expressed in at least some regions in the first pathology slide image included in the second pathology slide image, to thus generate information on the PD-L1 expression. In this example, the second pathology slide image may include a pathology slide image for the same region of the patient as the first pathology slide image. For example, the processor may remove an in-house control tissue region from the IHC-stained pathology slide image, divide the patient's tissue region into one or more regions of interest, and use the artificial neural network model for expression information generation to detect the location of tumor cells, lymphocytes, macrophages, and whether or not PD-L1 is expressed (e.g., PD-L1 negative, or PD-L1 positive), from the ROI, thereby calculating TPS and/or CPS.

In this example, the artificial neural network model for expression information generation may be a model trained to generate reference information on PD-L1 expression upon input of the reference pathology slide image. In order to generate/train the artificial neural network model for expression information generation, the processor may receive a plurality of learning pathology slide images and label information (or annotation information) for the plurality of learning pathology slide images. In this example, the label information for the learning pathology slide image may be the information generated by the user performing an annotation work.

Regarding the prediction of the response to the immune checkpoint inhibitor, the illustrated ROC curve graph 910 shows the ROC curves for specificity-sensitivity in the examples of using TPS calculated with the artificial neural network model for expression information generation (that is, "AI PD-L1 TPS"), using TPS calculated by a person (that is, "Human PD-L1 TPS"), and using TMB (that is, "Tumor Mutation Burden"). In the ROC curve graph 910, AUROC of AI PD-L1 TPS may be calculated as 0.784, AUROC of Human PD-L1 TPS may be calculated as 0.764, and AUROC of TMB may be calculated as 0.710. That is, when predicting the response to the immune checkpoint inhibitor, it has been proven that the AI PD-L1 TPS has the best performance with respect to specificity-sensitivity.

In an embodiment, the processor may generate a prediction result as to whether or not the patient responds to the immune checkpoint inhibitor, based on the information on the immune phenotype and the PD-L1 expression of at least some regions in the first pathology slide image. Specifically, when predicting whether or not a patient responds to the immune checkpoint inhibitor, the performance of the example of using the information on the immune phenotype and the PD-L1 expression together is superior to the example of individually using the immune phenotype determined through H&E-stained pathology slide image (e.g., first pathology slide image) and the information on the expression of the PD-L1 obtained from the IHC-stained pathology slide image (e.g., the second pathology slide image). In this example, the immune phenotype determined through the H&E-stained pathology slide image may refer to the representative immune phenotype of the pathology slide image, the immune phenotype of one or more regions of interest, the immune phenotype map, and the like.

According to the illustrated comparison of accuracy rate of AI-powered biomarker graph 920, when predicting the response to the immune checkpoint inhibitor, the accuracy when using the PD-L1 TPS calculated directly by a human ("Human PD-L1 TPS") corresponds to about 0.68, the accuracy when using TMB corresponds to about 0.69, the accuracy when using the immune phenotype ("AI H&E") corresponds to about 0.715, the accuracy when using the TPS calculated using the artificial neural network model for expression information generation ("AI PD-L1 TPS") corresponds to about 0.72. In addition, the accuracy when using Human PD-L1 TPS and AI PD-L1 TPS together ("Human PD-L1 TPS+AI PD-L1 TPS") corresponds to about 0.715, and the accuracy when using the accuracy when TMB and AI PD-L1 TPS together ("TMB+AI PD-L1 TPS") corresponds to about 0.72, and the accuracy when using AI H&E and AI PD-L1 TPS together ("AI H&E+AI PD-L1 TPS") corresponds to about 0.77. That is, when predicting the response to the immune checkpoint inhibitor, it has been proven that AI H&E+AI PD-L1 TPS has the best performance with respect to accuracy.

Figure 10:
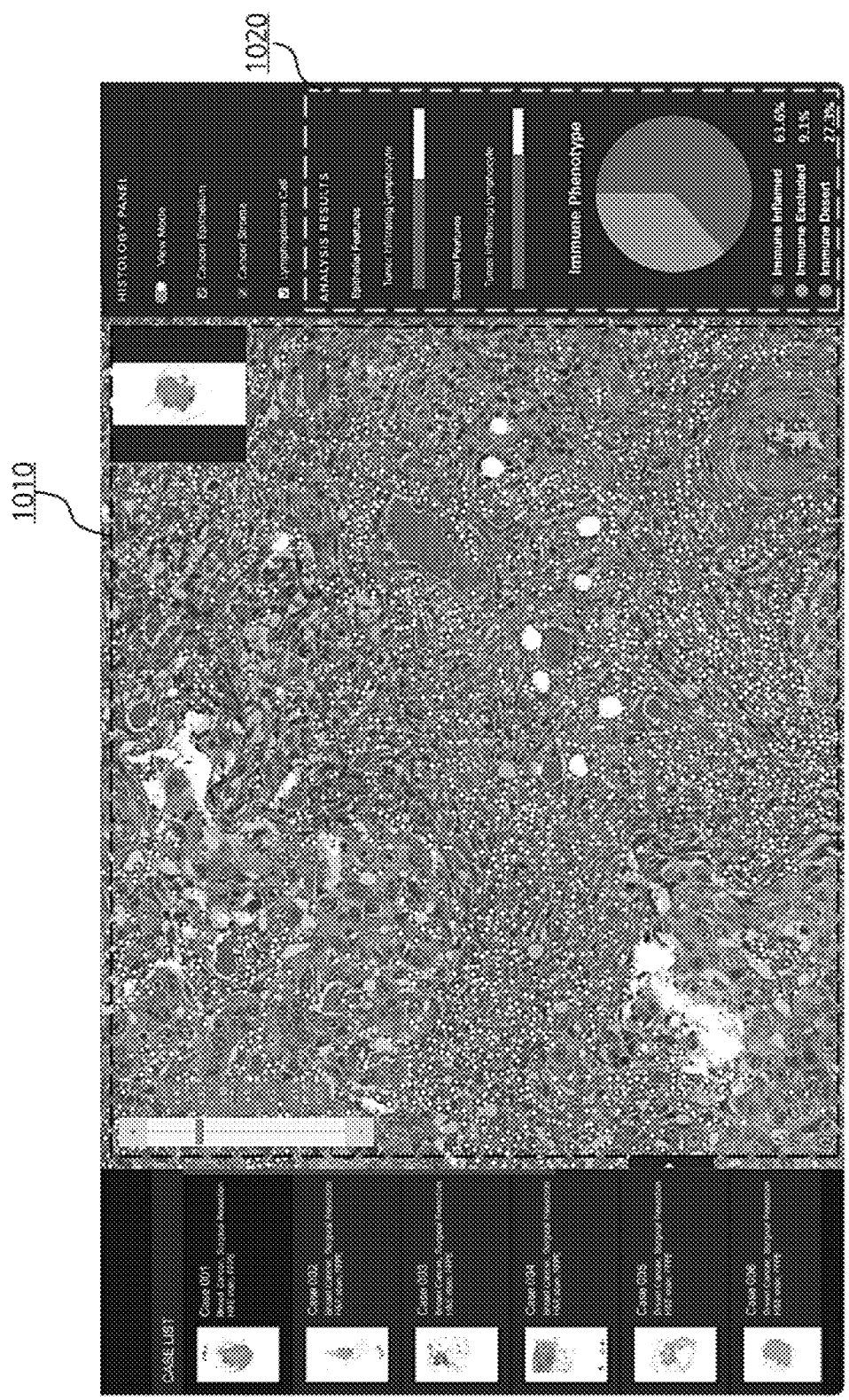
FIG. 10 is a diagram illustrating an example of outputting results generated in a process of predicting response or non-response to an immune checkpoint inhibitor according to an embodiment.

FIG. 10 is a diagram illustrating an example of outputting results generated in a process of predicting response or non-response to an immune checkpoint inhibitor according to an embodiment. In an embodiment, the processor (e.g., at least one processor of the information processing system terminal and/or at least one processor of the user terminal) may output at least one of a detection result for one or more target items, an immune phenotype of at least some regions in the first pathology slide image, information associated with the immune phenotype, a prediction result as to response or non-response to the immune checkpoint inhibitor, or a density of immune cells in at least some regions in the first pathology slide image. The information processing system (e.g., at least one processor of the information processing system) provides the user terminal with the results generated in the process of predicting response or non-response to the immune checkpoint inhibitor, and the user terminal may output the received results. For example, the user terminal may display the results on a display through a user interface, as illustrated.

In an embodiment, the user terminal may output the detection result for a target item 1010 for at least some regions in the pathology slide image and/or the first pathology slide image. For example, the user terminal may output the pathology slide image including the label information for each target item. The user terminal may output a pathology slide image, which may be displayed as a mask for a target item in units of areas, and displayed as a center point of a cell nucleus or a bounding box for a target item in units of cells. In another embodiment, the user terminal may visualize and output an immune phenotype map (or an immune phenotype feature map) and the like of the whole region of the pathology slide image or at least some regions in the first pathology slide image in an expression method such as a minimap, a heatmap, and/or a label map and the like. In still another embodiment, as a prediction result as to response or non-response to the immune checkpoint inhibitor for at least some regions in the first pathology slide image, the user terminal may visualize and output a response/non-respond score map in an expression method such as a heat map and/or a label map or the like based on the immune phenotype, inflamed score, respond score and/or non-respond score.

In still another embodiment, the user terminal may output a density of immune cells for each region, with respect to the whole and/or some regions of the pathology slide image. For example, the user terminal may output a numerical value or output a bar graph for the density of immune cells for each region, with respect to the whole and/or some regions of the pathology slide image. In still another embodiment, the user terminal may output a distribution of the immune phenotypes of a patient represented in the form of a circle plot. As illustrated, the user terminal may output an analysis result 1020 including the bar graph for the density of immune cells for each region and the circle graph for the distribution of immune phenotypes of the patient.

The user terminal may receive the results generated in the process of predicting response or non-response to the immune checkpoint inhibitor from the information processing system, and output the received results. Accordingly, the user can visually and intuitively recognize the results generated in the process of predicting response or non-response to the immune checkpoint inhibitor. In FIG. 10, the results generated in the prediction process are visually output through a user interface operating on the user terminal, but the embodiments are not limited thereto, and the generated results may be provided to the user in various ways.

FIGS. 11 to 15 are diagrams illustrating examples of outputting results generated in a process of predicting response or non-response to an immune checkpoint inhibitor according to another embodiment. In an embodiment, the information processing system (e.g., at least one processor of the information processing system) may generate and provide reports 1100, 1200, 1300, 1400, and 1500 including the results generated in the process of predicting response or non-response to the immune checkpoint inhibitor. The generated reports 1100, 1200, 1300, 1400, and 1500 may be provided as a file, data, text, image, and the like that can be output through the user terminal and/or output devices. In this example, the reports 1100, 1200, 1300, 1400, and 1500 may include at least one of the results described in FIG. 10.

In an embodiment, the information processing system may generate a report including a final score on responder/non-responder of the patient (e.g., a score between 0 and 1) (e.g., results indicating the probability that the patient is a responder and/or the probability that the patient is a non-responder). Additionally or alternatively, the information processing system may generate a report including information with respect to a cut-off value for determining the responder/non-responder. Additionally or alternatively, the information processing system may generate a report including an immune phenotype and/or distribution of TIL density (e.g., min, max, avg value) in the pathology slide image. For example, the information processing system may generate a report including the distribution, and min, max, avg values of the TIL density for each of the regions of interest classified into the three immune phenotype. Additionally or alternatively, the information processing system may generate a report including an immune phenotype map in which the region of interest in the pathology slide image is classified into the three immune phenotype.

The information processing system may perform some embodiments of the present disclosure on the pathology images (e.g., pathology slide images, and the like) before and/or after treatment with the immune checkpoint inhibitor, to identify acquired resistance mechanisms and provide a customized treatment policy for each resistance mechanism. For example, the processor may perform analysis using input data, such as a pathology image of a patient who is treated with the immune checkpoint inhibitor, the type of treatment administered to the patient, and the like, to predict a treatment outcome for each of the immune checkpoint inhibitors administered to the patient and/or other immune checkpoint inhibitor. In an embodiment, the information processing system may output information on at least one immune checkpoint inhibitor suitable for a patient from among a plurality of immune checkpoint inhibitors, based on the prediction result as to whether or not the patient will respond to the immune checkpoint inhibitors. For example, when the patient is determined to be a responder, the information processing system may generate a report including immune checkpoint inhibitor products and/or combinations of products that have high possibility of response.

Figure 11:
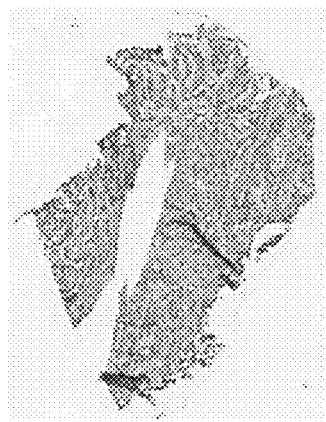
Figure 12:
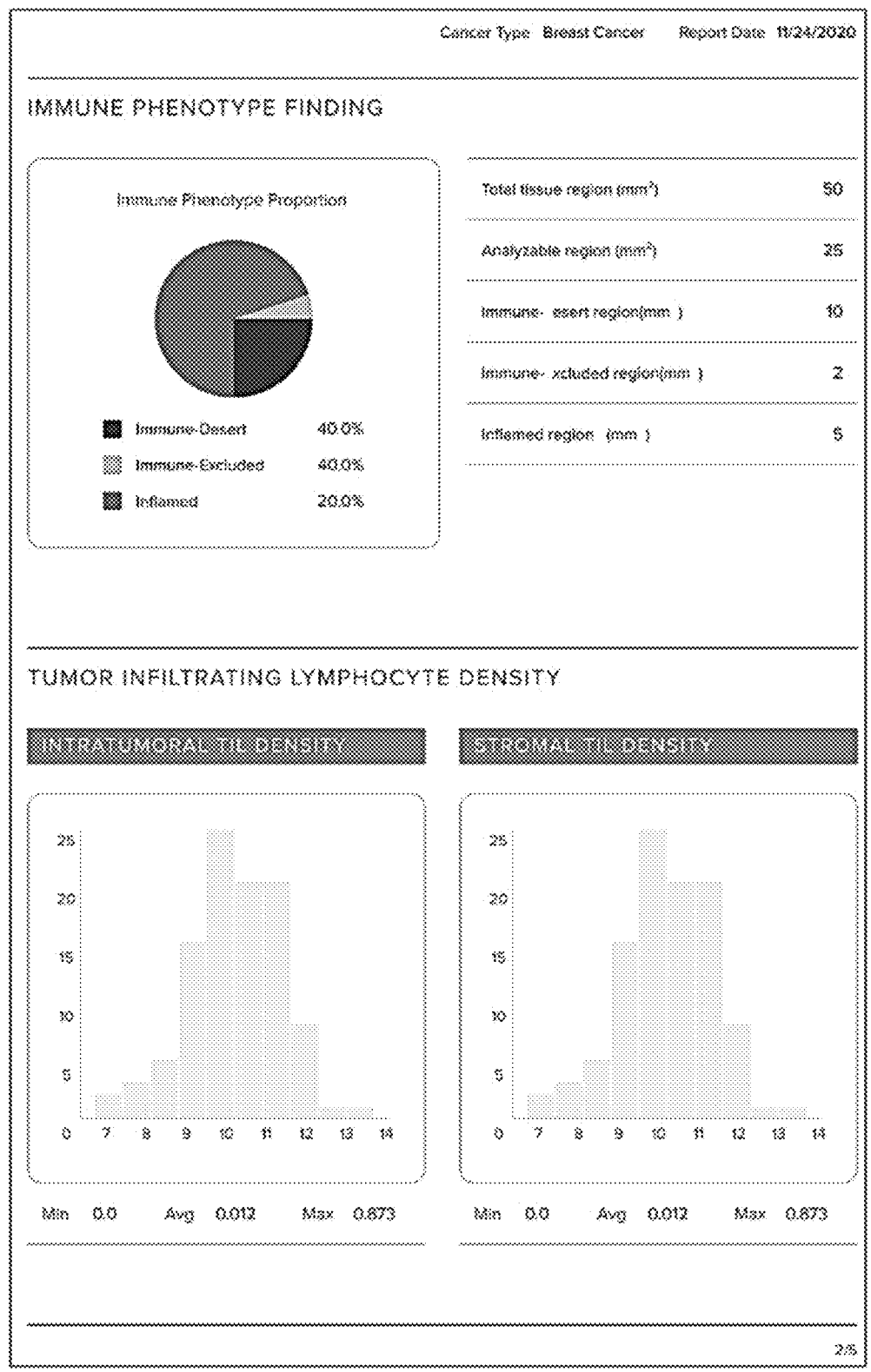
Figure 13:
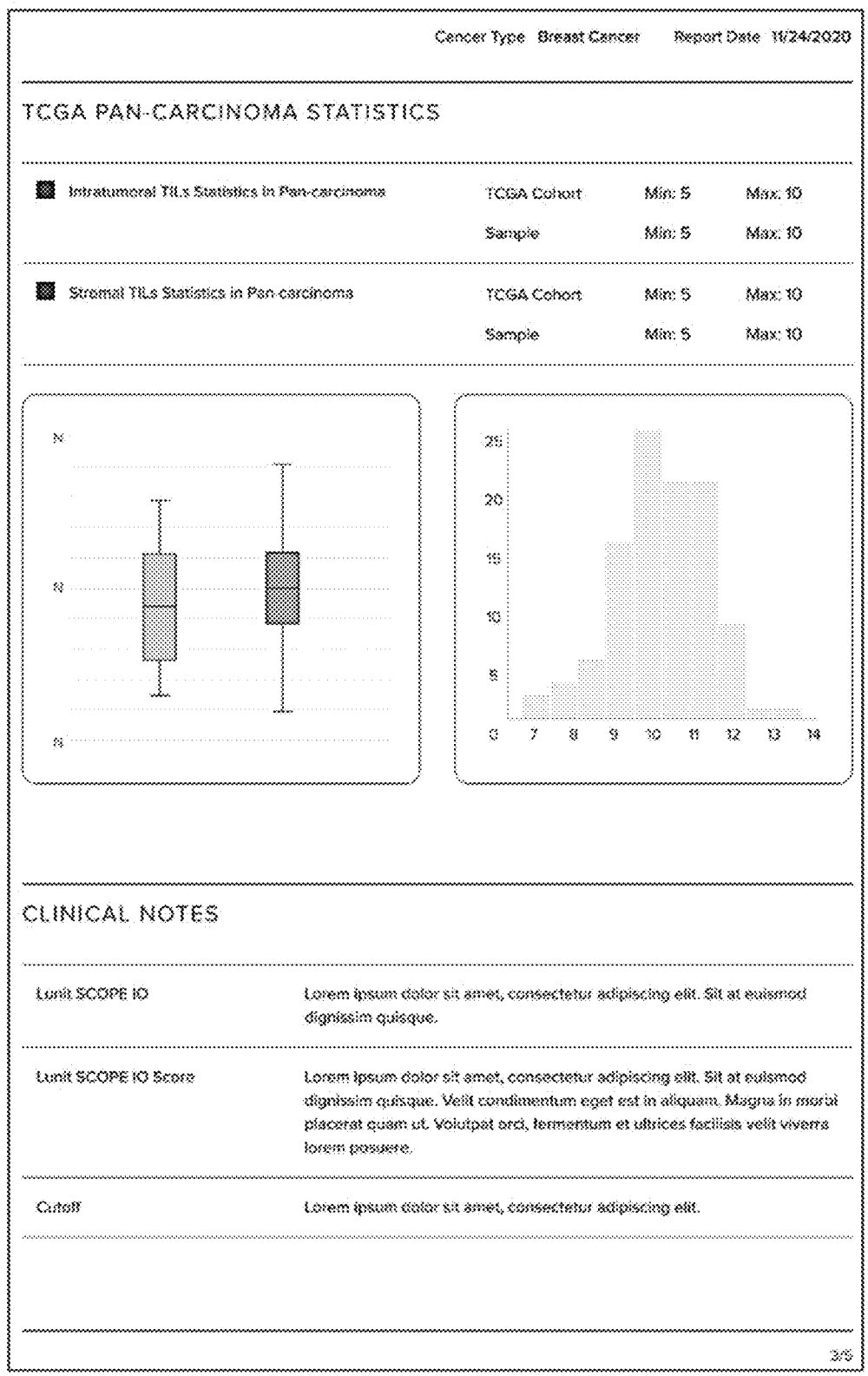
Figure 15:
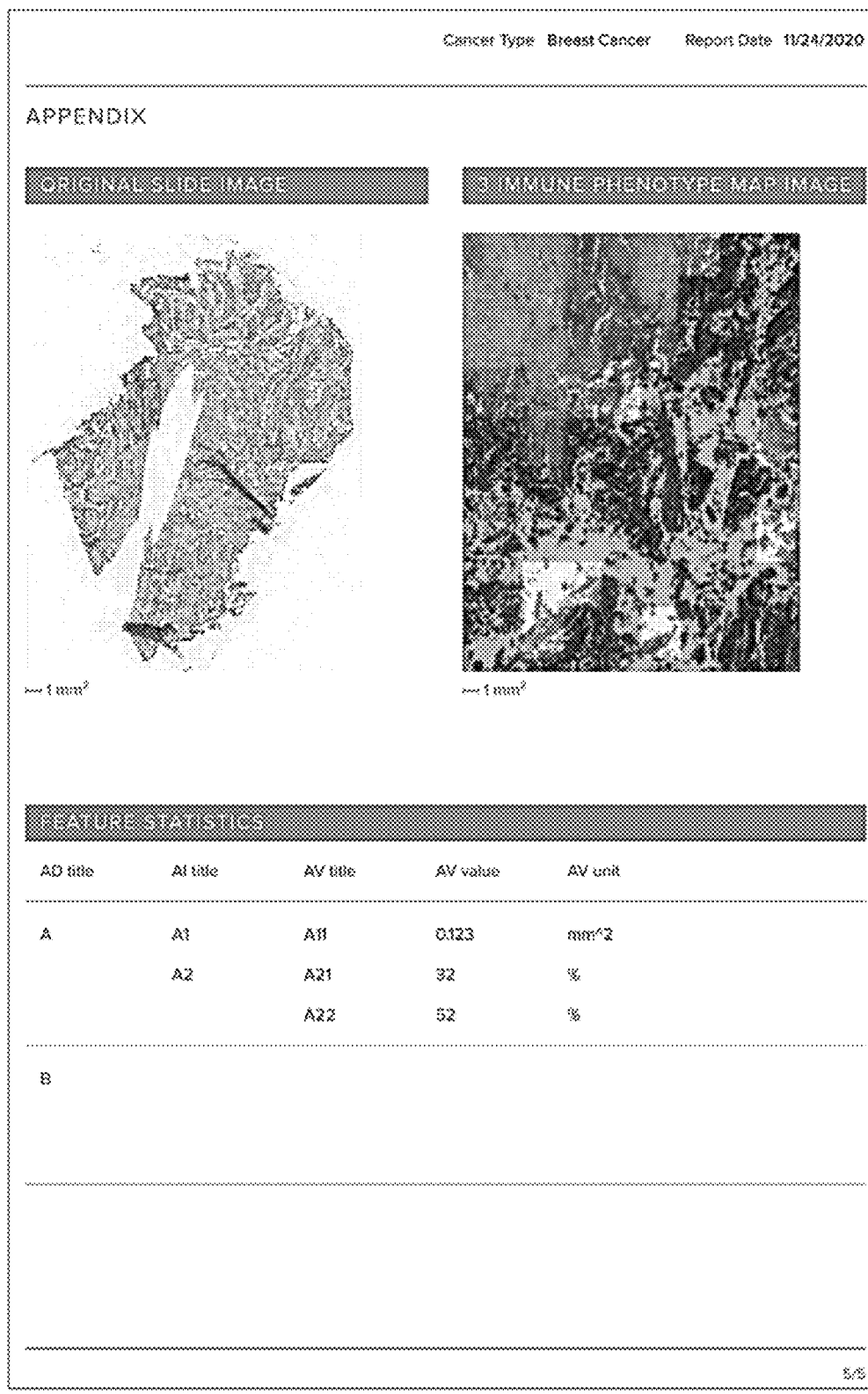

As shown in the reports 1100, 1200, 1300, 1400, and 1500, the results generated in the process of predicting response or non-response to the immune checkpoint inhibitor may be prepared in the form of a document including text and/or images and provided to the user. For example, as illustrated in FIG. 11, the report 1100 may include a pathology slide image, patient information, basic information, and/or prediction results (whether responder or non-responder). In addition, as illustrated in FIG. 12, the report 1200 may include graphs, numerical values, and information on TIL density (e.g., distribution of densities, and the like) indicating the ratio of immune phenotypes. In addition, as illustrated in FIG. 13, the report 1300 may include statistical results (e.g., TCGA PAN-CARCINOMA STATISTICS) and/or graphs indicating analysis results, clinical notes, and the like. As illustrated in FIG. 14, the report 1140 may include information on reference documents (e.g., academic references), and the like. As illustrated in FIG. 15, the report 1150 may include results (e.g., immune phenotype map images, feature statistics, and the like) generated in the prediction process and/or information used in the prediction process, and the like.

In FIGS. 11 to 15, the results generated in the prediction process are output in the form of a report, but embodiments are not limited thereto, and the generated results may be provided to the user in various ways.

Figure 16:
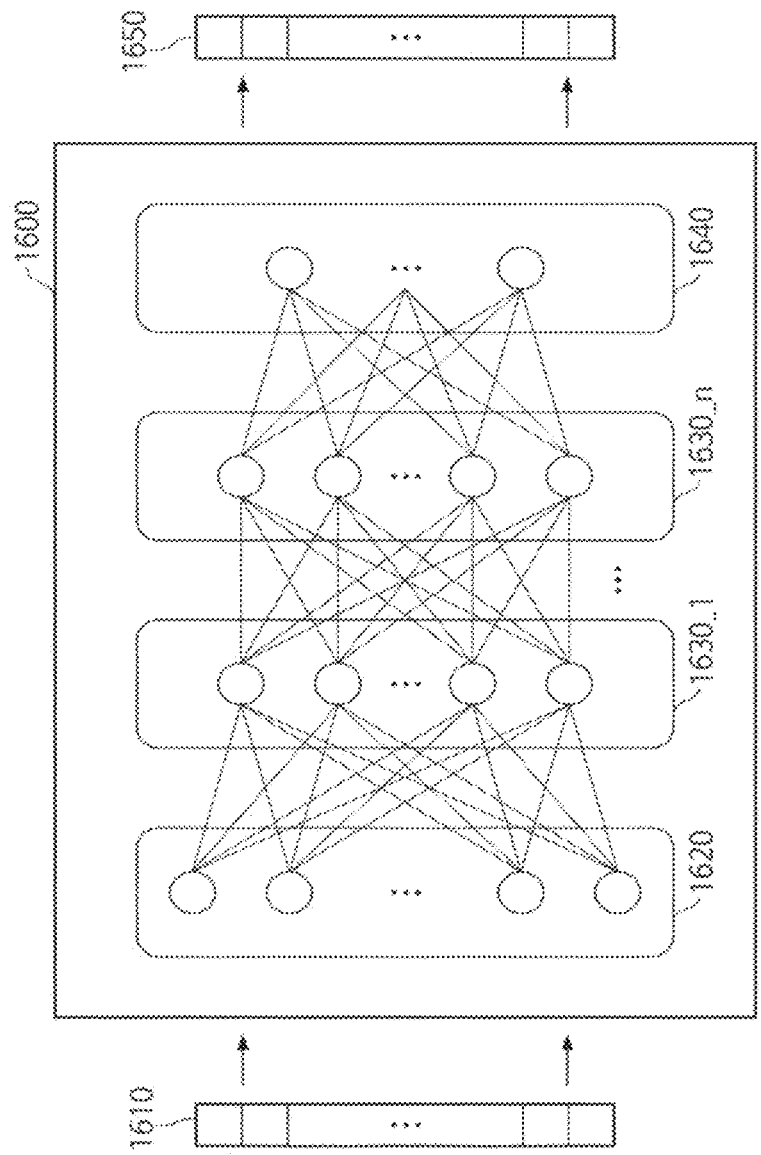
FIG. 16 is an exemplary diagram illustrating an artificial neural network model according to an exemplary embodiment.

FIG. 16 is an exemplary diagram illustrating an artificial neural network model 1600 according to an embodiment. In machine learning technology and cognitive science, an artificial neural network model 1600 as an example of the machine learning model refers to a statistical learning algorithm implemented based on a structure of a biological neural network, or to a structure that executes such algorithm.

According to an embodiment, the artificial neural network model 1600 may represent a machine learning model that acquires a problem solving ability by repeatedly adjusting the weights of synapses by the nodes that are artificial neurons forming the network through synaptic combinations as in the biological neural networks, thus training to reduce errors between a target output corresponding to a specific input and a deduced output. For example, the artificial neural network model 1600 may include any probability model, neural network model, and the like, that is used in artificial intelligence learning methods such as machine learning and deep learning.

According to an embodiment, the artificial neural network model 1600 may include an artificial neural network model configured to detect one or more target items from a pathology slide image being inputted. Additionally or alternatively, the artificial neural network model 1600 may include an artificial neural network model configured to determine at least one of the immune phenotype of at least some regions in the first pathology slide image or the information associated with the immune phenotype, based on an input of the feature for at least some regions in the first pathology slide image or the at least some regions in the first pathology slide image. Additionally or alternatively, the artificial neural network model 1600 may include an artificial neural network model configured to generate a prediction result as to whether or not a patient responds to an immune checkpoint inhibitor based on an immune phenotype map being inputted. Additionally or alternatively, the artificial neural network model 1600 may include an artificial neural network model configured to generate a prediction result as to whether or not a patient responds to the immune checkpoint inhibitor based on an immune phenotype feature map being inputted.

Additionally or alternatively, the artificial neural network model 1600 may include an artificial neural network model configured to generate information on the expression of the biomarker (e.g., PD-L1 expression, and the like) from a pathology slide image being inputted.

The artificial neural network model 1600 is implemented as a multilayer perceptron (MLP) formed of multiple nodes and connections between them. The artificial neural network model 1600 according to an embodiment may be implemented using one of various artificial neural network model structures including the MLP. As shown in FIG. 16, the artificial neural network model 1600 includes an input layer 1620 receiving an input signal or data 1610 from the outside, an output layer 1640 outputting an output signal or data 1650 corresponding to the input data, and (n) number of hidden layers 1630_1 to 1630_n (where n is a positive integer) positioned between the input layer 1620 and the output layer 1640 to receive a signal from the input layer 1620, extract the features, and transmit the features to the output layer 1640. In an example, the output layer 1640 receives signals from the hidden layers 1630_1 to 1630_n and outputs them to the outside.

The method of training the artificial neural network model 1600 includes the supervised learning that trains to optimize for solving a problem with inputs of teacher signals (correct answer), and the unsupervised learning that does not require a teacher signal. In an embodiment, the information processing system may train the artificial neural network model 1600 by supervised learning and/or unsupervised learning to detect one or more target items from a pathology slide image. For example, the information processing system may train the artificial neural network model 1600 by supervised learning to detect one or more target items from the pathology slide image by using a reference pathology slide image and label information for one or more reference target items. In another embodiment, the information processing system may train the artificial neural network model 1600 by supervised learning and/or unsupervised learning to determine at least one of the immune phenotype of at least some regions in the first pathology slide image or the information associated with the immune phenotype, based on the feature for the at least some regions in the first pathology slide image or the at least some regions in the first pathology slide image. For example, the information processing system may train the artificial neural network model 1600 by supervised learning to determine at least one of the immune phenotype of at least some regions in the reference pathology slide image or the information associated with the immune phenotype, based on the feature for the at least some regions in the reference pathology slide image or the at least some regions in the reference pathology slide image, using the feature for the at least some regions in the reference pathology slide image and the label information for at least one of the immune phenotype or the information associated with the immune phenotype of the at least some regions in the reference pathology slide image.

In still another embodiment, the information processing system may train the artificial neural network model 1600 by supervised and/or unsupervised learning to generate a prediction result as to whether or not a patient responds to the immune checkpoint inhibitor, based on the immune phenotype map or the immune phenotype feature map. For example, the information processing system may use the reference immune phenotype map (or the reference immune phenotype feature map) and the label information for the reference prediction result to train the artificial neural network model 1600 by supervised learning to generate a prediction result as to whether or not a patient responds to the immune checkpoint inhibitor based on the immune phenotype map (or the immune phenotype feature map). In still another embodiment, the information processing system may train the artificial neural network model 1600 by supervised and/or unsupervised learning to generate information on PD-L1 expression from the pathology slide image. For example, the information processing system may use the reference pathology slide image and label information for the reference information on the PD-L1 expression to train the artificial neural network model 1600 by supervised learning to generate information on the PD-L1 expression from the pathology slide image.

The artificial neural network model 1600 trained as described above may be stored in a memory (not illustrated) of the information processing system, and in response to an input for the pathology slide image received from the communication module and/or the memory, may detect one or more target items in the pathology slide image. Additionally or alternatively, in response to an input for the feature for each of the at least some regions in the first pathology slide image or for the at least some regions in the first pathology slide image, the artificial neural network model 1600 may determine the immune phenotype of the at least some regions in the first pathology slide image or the information associated with the immune phenotype. Additionally or alternatively, in response to an input for the immune phenotype map or the immune phenotype feature map, the artificial neural network model 1600 may generate a prediction result as to whether or not a patient responds to the immune checkpoint inhibitor. Additionally or alternatively, in response to an input for the pathology slide image received from the communication module and/or the memory, the artificial neural network model 1600 may generate information on the expression of a biomarker.

According to an embodiment, the input variable of the artificial neural network model for detecting the target item and/or the artificial neural network model for generating information on the expression of the biomarker (e.g., PD-L1 expression, and the like) may be one or more pathology slide images (e.g., H&E-stained pathology slide images, IHC-stained pathology slide images). For example, the input variable input to the input layer 1620 of the artificial neural network model 1600 may be the image vector 1610 which may be one or more pathology slide images configured as one vector data element. The output variable output from the output layer 1640 of the artificial neural network model 1600 in response to the input of the image may be a vector 1650 representing or characterizing one or more target items detected in the pathology slide image. Additionally or alternatively, the output variable output from the output layer 1640 of the artificial neural network model 1600 may be a vector 1650 representing or characterizing the information on the expression of biomarker generated from the pathology slide image. That is, the output layer 1640 of the artificial neural network model 1600 may be configured to output one or more target items detected in the pathology slide image and/or the vector indicating or characterizing information on the expression of biomarker generated from the pathology slide image. In the present disclosure, the output variable of the artificial neural network model 1600 is not limited to the types described above, and may include any information/data representing information on one or more target items detected in the pathology slide image and/or the expression of biomarker generated from the pathology slide image.

In another embodiment, the input variable for the machine learning model for determining the immune phenotype of at least some regions in the reference pathology slide image, that is, the input variable for the artificial neural network model 1600 may be the feature for at least some regions in the first pathology slide image or the at least some regions in the first pathology slide image. For example, the input variable input to the input layer 1620 of the artificial neural network model 1600 may be the feature for at least some regions in the first pathology slide image or the numerical vector 1610 which may be at least some regions in the first pathology slide image configured as one vector data element. In response to this input, the output variable output from the output layer 1640 of the artificial neural network model 1600 may be a vector 1650 representing or characterizing the immune phenotype of each of at least some regions in the first pathology slide image or the information associated with the immune phenotype. In the present disclosure, the output variable of the artificial neural network model 1600 is not limited to the type described above, and may include any information/data representing or characterizing the immune phenotype of each of at least some regions in the first pathology slide image. In still another embodiment, the input variable of the machine learning model, that is, the input variable of the artificial neural network model 1600 for generating a prediction result as to whether or not a patient responds to the immune checkpoint inhibitor may be the immune phenotype map or the immune phenotype feature map. For example, the input variable input to the input layer 1620 of the artificial neural network model 1600 may be the numerical vector 1610 which may be the immune phenotype map or the immune phenotype feature map configured as one vector data element and/or image data. In response to an input for the immune phenotype map or the immune phenotype feature map, the output variable output from the output layer 1640 of the artificial neural network model 1600 may be a vector 1650 representing or characterizing the prediction result as to whether or not a patient responds to the immune checkpoint inhibitor. In the present disclosure, the output variable of the artificial neural network model 1600 is not limited to the type described above, and may include any information/data representing the prediction result as to whether or not the patient responds to the immune checkpoint inhibitor. In addition, the output layer 1640 of the artificial neural network model 1600 may be configured to output a vector representing the reliability and/or accuracy of the output prediction result and the like.

As described above, the input layer 1620 and the output layer 1640 of the artificial neural network model 1600 are respectively matched with a plurality of output variables corresponding to a plurality of input variables, and the synaptic values between nodes included in the input layer 1620, the hidden layers 1630_1 to 1630_n, and the output layer 1640 are adjusted, so that by training, a correct output corresponding to a specific input can be extracted. Through this training process, the features hidden in the input variables of the artificial neural network model 1600 may be confirmed, and the synaptic values (or weights) between the nodes of the artificial neural network model 1600 may be adjusted so as to reduce the errors between the output variable calculated based on the input variable and the target output. By using the artificial neural network model 1600 trained in this way, in response to the input pathology slide image, a detection result for target item and/or information on PD-L1 expression may be output. Additionally or alternatively, by using the artificial neural network model 1600, in response to an input of the feature for at least some regions in one or more reference pathology slide images or the at least some regions in the reference pathology slide images, at least one of the immune phenotype of one or more regions of interest or the information associated with the immune phenotype may be output. Additionally or alternatively, by using the artificial neural network model 1600, in response to an input of the immune phenotype map, a prediction result as to whether or not the patient responds to the immune checkpoint inhibitor may be output.

Figure 17:
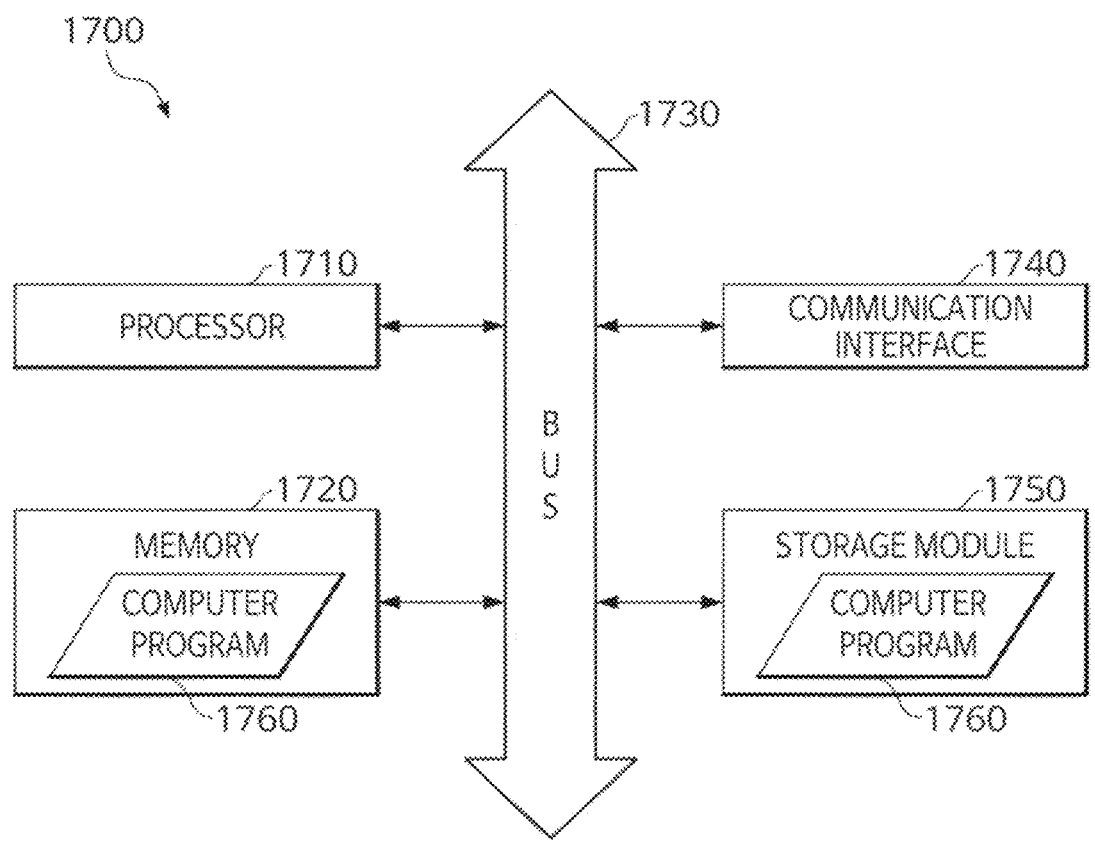
FIG. 17 is a configuration diagram illustrating an exemplary system providing a prediction result of a response to an immune checkpoint inhibitor according to an embodiment.

FIG. 17 is a configuration diagram illustrating an exemplary system 100 providing a prediction result of a response to an immune checkpoint inhibitor according to an embodiment. As illustrated, the information processing system 100 may include one or more processors 1710, a bus 1730, a communication interface 1740, a memory 1720 for loading a computer program 1760 to be executed by the processors 1710, and a storage module 1750 for storing the computer program 1760. However, only the components related to the embodiment of the present disclosure are illustrated in FIG. 17. Accordingly, those skilled in the art to which the present disclosure pertains will be able to recognize that other general-purpose components may be further included in addition to the components shown in FIG. 17.

The processors 1710 control the overall operation of components of the information processing system 100. The processors 1710 may be configured to include a central processing unit (CPU), a micro processor unit (MPU), a micro controller unit (MCU), a graphic processing unit (GPU), or any type of processor well known in the technical field of the present disclosure. In addition, the processors 1710 may perform an arithmetic operation on at least one application or program for executing the method according to the embodiments of the present disclosure. The information processing system 100 may include one or more processors.

The memory 1720 may store various types of data, commands, and/or information. The memory 1720 may load one or more computer programs 1760 from the storage module 1750 in order to execute a method/operation according to various embodiments of the present disclosure. The memory 1720 may be implemented as a volatile memory such as RAM, but the technical scope of the present disclosure is not limited thereto.

The bus 1730 may provide a communication function between components of the information processing system 100. The bus 1730 may be implemented as various types of buses such as an address bus, a data bus, a control bus, or the like.

The communication interface 1740 may support wired/wireless Internet communication of the information processing system 100. In addition, the communication interface 1740 may support various other communication methods in addition to the Internet communication. To this end, the communication interface 1740 may be configured to include a communication module well known in the technical field of the present disclosure.

The storage module 1750 may non-temporarily store one or more computer programs 1760. The storage module 1750 may be configured to include a nonvolatile memory such as a read only memory (ROM), an erasable programmable ROM (EPROM), an electrically erasable programmable ROM (EEPROM), a flash memory, and the like, a hard disk, a detachable disk, or any type of computer-readable recording medium well known in the art to which the present disclosure pertains.

The computer program 1760 may include one or more instructions that, when loaded into the memory 1720, cause the processors 1710 to perform an operation/method in accordance with various embodiments of the present disclosure. That is, the processors 1710 may perform operations/methods according to various embodiments of the present disclosure by executing one or more instructions.

For example, the computer program 1760 may include one or more instructions for causing the following operations to be performed: receiving a first pathology slide image; detecting one or more target items in the first pathology slide image; determining at least one of an immune phenotype of at least some regions in the first pathology slide image or information associated with the immune phenotype, based on the detection result for the one or more target items; generating a prediction result as to whether or not a patient associated with the first pathology slide image responds to an immune checkpoint inhibitor, based on at least one of the immune phenotype of the at least some regions in the first pathology slide image or the information associated with the immune phenotype, and the like. In this case, a system for predicting a response to the immune checkpoint inhibitor according to some embodiments of the present disclosure may be implemented through the information processing system 100.

The above description of the present disclosure is provided to enable those skilled in the art to make or use the present disclosure. Various modifications of the present disclosure will be readily apparent to those skilled in the art, and the general principles defined herein may be applied to various modifications without departing from the spirit or scope of the present disclosure. Thus, the present disclosure is not intended to be limited to the examples described herein but is intended to be accorded the broadest scope consistent with the principles and novel features disclosed herein.

Although example implementations may refer to utilizing aspects of the presently disclosed subject matter in the context of one or more standalone computer systems, the subject matter is not so limited, and they may be implemented in conjunction with any computing environment, such as a network or distributed computing environment. Furthermore, aspects of the presently disclosed subject matter may be implemented in or across a plurality of processing chips or devices, and storage may be similarly influenced across a plurality of devices. Such devices may include PCs, network servers, and handheld devices.

Although the present disclosure has been described in connection with some embodiments herein, it should be understood that various modifications and changes can be made without departing from the scope of the present disclosure, which can be understood by those skilled in the art to which the present disclosure pertains. In addition, such modifications and changes should be considered within the scope of the claims appended herein.

What is claimed is:

1. An information processing system comprising:
a memory storing one or more instructions; and
at least one processor configured to execute the stored one or more instructions to:

detect target items including immune cells, tumor cells, a cancer area and a stroma area in an H&E stained pathology slide image using an artificial neural network model,
  inputting the H&E stained pathology slide image into the artificial neural network model;
  detecting, with the artificial neural network model, the immune cells and the tumor cells in the H&E stained pathology slide image as the target items in units of cells; and
  detecting, with the artificial neural network model, the cancer area and the stroma area in the H&E stained pathology slide image as the target items in units of areas;
determine at least one region of interest (ROI) of a predetermined size in the H&E stained pathology slide image;
calculate, for each of the at least one ROI, at least one of a density of the immune cells in the cancer area in the ROI or a density of the immune cells in the stroma area in the ROI;
generate, based on the calculated density of the immune cells, a prediction result as to whether or not a patient associated with the H&E stained pathology slide image responds to a treatment, by:
  determining an immune phenotype of the at least one ROI by comparing at least one of the density of the immune cells in the cancer area in the ROI or the density of the immune cells in the stroma area in the ROI with a threshold density;
  calculating an inflamed score for the patient based on a ratio of ROIs having an immune phenotype of a specific class in the at least one ROI; and
  classifying the patient associated with the H&E stained pathology slide image as a responder or a non-responder to the treatment based on the inflamed score; and
output the prediction result.

2. The information processing system according to claim 1,
wherein the stored one or more instructions are configured to cause the at least one processor to generate the prediction result by determining, based on the calculated density of the immune cells, immune phenotypes of each of the at least one ROI in the H&E stained pathology slide image, and
wherein the immune phenotypes are determined as at least one of a plurality of classes, each of which is indicative of an immune environment of the ROI.

3. The information processing system according to claim 2, wherein the stored one or more instructions are configured to cause the at least one processor to generate the prediction result by:
  determining, based on the immune phenotypes of each of the at least one ROI, a most common immune phenotype included in the H&E stained pathology slide image; and
  generating, based on the most common immune phenotype included in the H&E stained pathology slide image, the prediction result as to whether or not the patient responds to the treatment.

4. The information processing system according to claim 2, wherein the stored one or more instructions are configured to cause the at least one processor to provide a report comprising at least one of the H&E stained pathology slide image, the prediction result as to whether or not the patient responds to the treatment, a graph showing a ratio of the immune phenotypes, and information on the density of the immune cells.

5. The information processing system according to claim 2, wherein the stored one or more instructions are configured to cause the at least one processor to output an immune phenotype map representing information on the immune phenotypes of each of the at least one ROI on the H&E stained pathology slide image.

6. The information processing system according to claim 1, wherein the stored one or more instructions are configured to cause the at least one processor to output at least one of the detected immune cells, the detected tumor cells, the detected cancer area, or the detected stroma area on the H&E stained pathology slide image.

7. A method, performed by at least one computing device, for predicting a response to a treatment, comprising:
  detecting target items including immune cells, tumor cells, a cancer area and a stroma area in an H&E stained pathology slide image using artificial neural network model, by:
    inputting the H&E stained pathology slide image into the artificial neural network model;
    detecting, with the artificial neural network model, the immune cells and the tumor cells in the H&E stained pathology slide image as the target items in units of cells; and
    detecting, with the artificial neural network model, the cancer area and the stroma area in the H&E stained pathology slide image as the target items in units of areas;
  determining at least one region of interest (ROI) of a predetermined size in the H&E stained pathology slide image;
  calculating, for each of the at least one ROI in the H&E stained pathology slide image, at least one of a density of the immune cells in the cancer area in the ROI or a density of the immune cells in the stroma area in the ROI;
  generating, based on the calculated density of the immune cells, a prediction result as to whether or not a patient associated with the H&E stained pathology slide image responds to the treatment, by:
    determining an immune phenotype of the at least one ROI by comparing at least one of the density of the immune cells in the cancer area in the ROI or the density of the immune cells in the stroma area in the ROI with a threshold density; and
    calculating an inflamed score for the patient based on a ratio of ROIs having an immune phenotype of a specific class in the at least one ROI; and
    classifying the patient associated with the H&E stained pathology slide image as a responder or a non-responder to the treatment based on the inflamed score; and
  outputting the prediction result.

8. The method according to claim 7,
wherein generating comprises determining, based on the calculated density of the immune cells, immune phenotypes of each of the at least one ROI in the H&E stained pathology slide image, and
wherein the immune phenotypes are determined based on at least one of a plurality of classes, each of which is indicative of an immune environment of the ROI.

9. The method according to claim 8, wherein the determining immune phenotypes comprises:

based on the density of the immune cells in the cancer area in a specific ROI is-being equal to or greater than a first threshold density, determining an immune phenotype of the specific ROI in the H&E stained pathology slide image to be immune inflamed, based on the density of the immune cells in the cancer area in the specific ROI is-being less than the first threshold density and the density of the immune cells in the stroma area in the specific ROI is equal to or greater than a second threshold density, determining the immune phenotype of the specific ROI in the H&E stained pathology slide image to be immune excluded, and based on the density of the immune cells in the cancer area in the specific ROI is-being less than the first threshold density and the density of the immune cells in the stroma area in the specific ROI is less than the second threshold density, determining the immune phenotype of the specific ROI in the H&E stained pathology slide image to be immune deserted.

10. The method according to claim 8, wherein the generating further comprises:

determining, based on the immune phenotypes of each of the at least one ROI, a most common immune phenotype included in the H&E stained pathology slide image; and generating, based on the most common immune phenotype included in the H&E stained pathology slide image, the prediction result as to whether or not the patient responds to the treatment.

11. The method according to claim 8, further comprising:

providing a report comprising at least one of the H&E stained pathology slide image, the prediction result as to whether or not the patient responds to the treatment, a graph showing a ratio of the immune phenotypes, and information on the density of the immune cells.

12. The method according to claim 8, further comprising:

outputting an immune phenotype map representing information on the immune phenotypes of each of the at least one ROI on the H&E stained pathology slide image.

13. The method according to claim 7, further comprising:

outputting at least one of the detected immune cells, the detected tumor cells, the detected cancer area, or the detected stroma area on the H&E stained pathology slide image.

14. A non-transitory computer-readable recording medium storing a computer program for executing, on a computer, the method for predicting the response to the treatment according to claim 7.

* * * * *